(12) United States Patent
Takeuchi et al.

(10) Patent No.: US 11,417,189 B2
(45) Date of Patent: Aug. 16, 2022

(54) INFORMATION PROCESSING APPARATUS AND METHOD, STORAGE MEDIUM, AND MONITORING SYSTEM

(71) Applicant: CANON KABUSHIKI KAISHA, Tokyo (JP)

(72) Inventors: Koichi Takeuchi, Yokohama (JP); Masakazu Matsugu, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 45 days.

(21) Appl. No.: 16/363,192

(22) Filed: Mar. 25, 2019

(65) Prior Publication Data
US 2019/0304284 A1    Oct. 3, 2019

(30) Foreign Application Priority Data
Mar. 29, 2018 (JP) .............................. JP2018-065498

(51) Int. Cl.
*G08B 21/04* (2006.01)
*A61B 5/00* (2006.01)

(52) U.S. Cl.
CPC ........ *G08B 21/0423* (2013.01); *A61B 5/0013* (2013.01); *G08B 21/043* (2013.01); *G08B 21/0415* (2013.01)

(58) Field of Classification Search
CPC ............ G08B 21/0423; G08B 21/0415; G08B 21/043; G08B 21/0476; A61B 5/0013;
(Continued)

(56) References Cited

U.S. PATENT DOCUMENTS 9,147,130 B2    9/2015  Saruta et al.
9,697,441 B2    7/2017  Mitarai et al.
(Continued)

FOREIGN PATENT DOCUMENTS

JP    2012071004 A    4/2012
JP    2014149771 A    8/2014
(Continued)

OTHER PUBLICATIONS

Notice of Reasons for Refusal issued by the Japan Patent Office dated May 9, 2022 in corresponding JP Patent Application No. 2018-065498, with English translation.

*Primary Examiner* — Brian Wilson
(74) *Attorney, Agent, or Firm* — Carter, DeLuca & Farrell LLP

(57) ABSTRACT

An apparatus for monitoring an object in a video received from at least one camera, comprises a storage unit storing a plurality of pieces of rule information each defining a condition of an object and a movement of the object to be observed in the condition, an input unit inputting information for identifying a monitored object and information representing a condition of the object, an acquiring unit acquiring rule information defining a movement to be observed for the object by referring to the storage unit based on the information representing the condition of the object, which is input by the input unit; and a monitoring unit determining whether the object in the video exhibits the movement to be observed, which is represented by the rule information acquired by the acquiring unit, and output a result of the determination.

20 Claims, 14 Drawing Sheets

(58) Field of Classification Search
CPC ....... A61B 5/18; A61B 5/7435; A61B 5/1113; A61B 5/1128
See application file for complete search history.

(56) References Cited

U.S. PATENT DOCUMENTS

| | | | |
|---|---|---|---|
| 9,792,689 B2 | 10/2017 | Shiozaki et al. | |
| 10,319,477 B1* | 6/2019 | Bill | G16H 50/30 |
| 2010/0241464 A1* | 9/2010 | Amigo | A61B 5/1123 |
| | | | 705/4 |
| 2012/0182155 A1* | 7/2012 | Sato | B25J 9/1674 |
| | | | 340/686.6 |
| 2013/0051687 A1 | 2/2013 | Kuroki et al. | |
| 2013/0082837 A1* | 4/2013 | Cosentino | G06F 19/3418 |
| | | | 340/539.12 |
| 2016/0026853 A1* | 1/2016 | Wexler | G06F 16/532 |
| | | | 382/103 |
| 2017/0199899 A1 | 7/2017 | Kuroki et al. | |
| 2018/0068461 A1 | 3/2018 | Shiozaki et al. | |
| 2019/0205630 A1* | 7/2019 | Kusens | G06T 7/73 |
| 2019/0313948 A1* | 10/2019 | Matsunaga | H04N 7/183 |

FOREIGN PATENT DOCUMENTS

| | | |
|---|---|---|
| JP | 5845506 B | 1/2016 |
| WO | 2007138811 A | 12/2007 |

* cited by examiner

FIG. 2

| CONDITION RULE | | |
|---|---|---|
| MEDICAL INFORMATION | | |

U21-1
- ✓ THE RIGHT LEG IS BROKEN
- ☐ THE LEFT LEG IS BROKEN
- ☐ CANNOT ROLL OVER BY HIMSELF/HERSELF

U21-2  (NEW MEDICAL INFORMATION)  [ADD]

| CONDITION | DANGER LEVEL |
|---|---|
| WALK WITHOUT CRUTCHES | 70 |
| WALK WITH CRUTCHES | 30 |
| HIT OF THE RIGHT LEG AGAINST AN OBJECT | 80 |

U21-3 (table above)

U21-4  (NEW CONDITION)  [ADD]

U21-5  DANGER LEVEL OF DETECTION TARGET  50

FIG. 3

| | ELECTRONIC MEDICAL CHART INPUT | |
|---|---|---|
| U1-1 — NAME | TANAKA TARO | PATIENT ID: P00123 |
| | | U1-6 |
| U1-2 — SEX | MALE ▽ | |
| U1-3 — AGE | 74 ▽ | |
| U1-4 — CARE INSTRUCTION | IMMEDIATELY AFTER SURGERY ON THE RIGHT ARM, KEEP THE RIGHT ARM AT REST AND TAKE A MEDICINE AFTER MEALS | |
| | U1-5 — OK    CANCEL | |

FIG. 11

WORK INSTRUCTION DATA

WS-1　　WS-2　　　　　　　　　　　WS-3

| ORDER | WORK | REMARKS |
|---|---|---|
| 1 | PLACE A BOX UNDER A TUBE | — |
| 2 | EXTRACT A SACK FROM THE BOX | — |
| 3 | ATTACH THE SACK TO THE TUBE | — |
| 4 | INKJET A POWDER | NEEDED TIME: ABOUT 15 MIN |
| 5 | DETACH THE SACK | REMOVE STATIC ELECTRICITY IN ADVANCE |
| 6 | TIE THE MOUTH OF THE SACK | — |
| 7 | PACK THE SACK IN THE BOX | — |
| 8 | PLACE THE BOX ON A LANE | USE CARRYING TOOL BECAUSE OF THE HEAVY LOAD |

F I G. 12
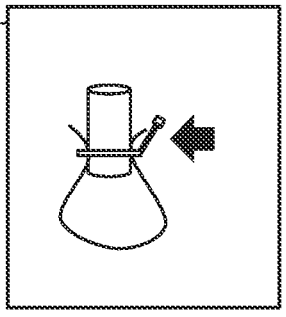

INFORMATION PROCESSING APPARATUS AND METHOD, STORAGE MEDIUM, AND MONITORING SYSTEM

BACKGROUND OF THE INVENTION

Field of the Invention

The present invention relates to an information processing apparatus and method, a storage medium, and a monitoring system.

Description of the Related Art

In recent years, a method of detecting a dangerous or abnormal condition from a video is widely used for various application purposes. For example, as representative application purposes, a dangerous condition of a patient or a resident is detected from a video of a camera installed in a hospital ward or a care facility, or an error in a work is detected from a video of a camera installed in a factory.

Of the conditions of a person, an object, a situation, and the like, a condition that is the detection target of a detecting system is called a target condition in this specification. Detection based on a video is executed by a specific processing method corresponding to a target condition. For example, if "a condition in which an object is moving" is the target condition, a processing method of, for example, performing processing such as object detection or motion vector estimation and performing detection if the result exceeds a set threshold is executed. Such a definition of a condition such as a series of processing methods or a parameter concerning detection based on a video will be referred to as a detection rule in this specification.

The detection rule is defined in correspondence with a target condition. However, an appropriate target condition sometime changes depending on a person, an object, a situation, or the like. For example, in a facility where only persons concerned can enter, an entry of an outsider is a target condition, but an entry of a person concerned is not a target condition. In this case, the detection rule needs to be changed in accordance with the target person or situation.

Japanese Patent No. 5845506 (to be referred to as a literature 1 hereinafter) discloses a method of detecting a target condition set for each person. In this method, a person and the situation of the person are estimated from a video. Next, the estimated situation is compared with a target condition set for the person, and if these match, detection is performed. This enables appropriate detection even in a case in which the target condition changes for each person.

International Publication No. 2007/138811 (to be referred to as a literature 2 hereinafter) discloses a method of acquiring the action authority level of a person or a vehicle and detecting a target condition set for the action authority level. This method also enables detection in a case in which the target condition changes for each person or vehicle.

In the method of literature 1, a target condition set for each person is detected from a video. However, there is neither a description nor a suggestion about setting a target condition. Hence, the method can hardly be applied in a case in which target condition setting itself is difficult because, for example, a target condition corresponding to a person is not self-evident or varies.

In the method of literature 2, a target condition set for each action authority level is detected from a video. However, as in literature 1, since the method does not set a target condition, there exists the same problem.

SUMMARY OF THE INVENTION

The present invention provides a technique capable of easily setting a movement of a target condition, which should be observed, even in a case in which it is difficult to set a condition of an object, and monitoring the movement.

According to an aspect of the invention, there is provided an information processing apparatus for monitoring an object in a received video, comprising: a storage unit configured to store a plurality of pieces of rule information each defining a condition of an object and a movement of the object to be observed in the condition; an input unit configured to input information for identifying a monitored object and information representing a condition of the monitored object; an acquiring unit configured to acquire rule information defining a movement to be observed for the monitored object by referring to the storage unit based on the information representing the condition of the monitored object, which is input by the input unit; and a monitoring unit configured to determine whether the monitored object in the received video exhibits the movement to be observed, which is represented by the rule information acquired by the acquiring unit, and output a result of the determination.

According to the present invention, it is possible to easily set a movement of a target condition, which should be observed, even in a case in which it is difficult to set a condition of an object, and monitor the movement.

Further features of the present invention will become apparent from the following description of exemplary embodiments (with reference to the attached drawings).

BRIEF DESCRIPTION OF THE DRAWINGS

FIG. 2 is a view showing an example of the GUI of a condition rule setting unit according to the first embodiment;

FIG. 3 is a view showing an example of the GUI of a data input unit according to the first embodiment;

FIG. 11 is a view showing an example of work instruction data according to the fourth embodiment;

FIG. 12 is a view showing an example of work instruction data according to the fourth embodiment;

DESCRIPTION OF THE EMBODIMENTS

Figure 1:
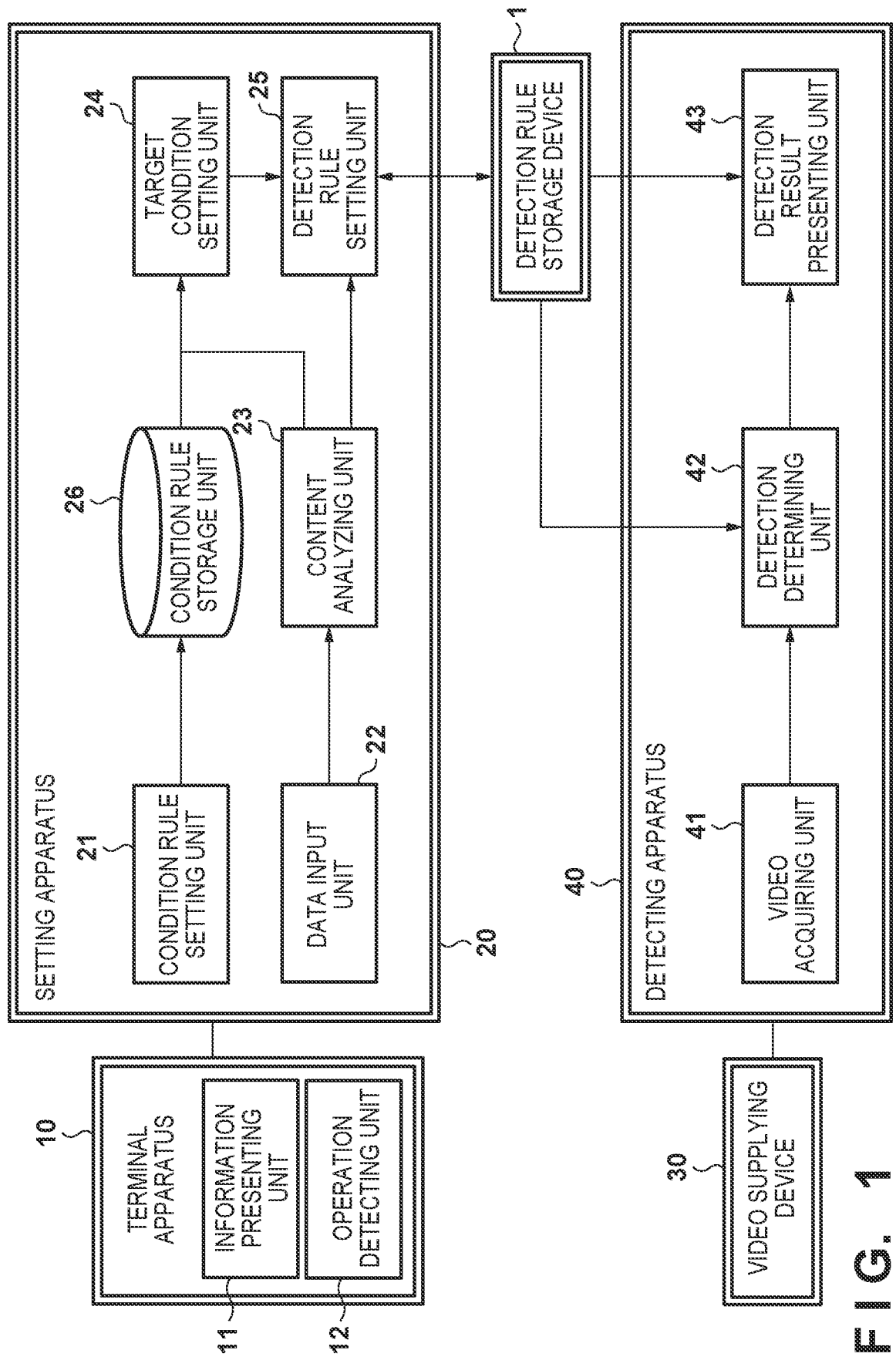
FIG. 1 is a block diagram of the arrangement of a watching system according to the first embodiment.

Embodiments according to the present invention will now be described in detail with reference to the accompanying drawings. Note that in each embodiment to be explained below, an example of application to a watching system will be described. The watching system according to this embodiment defines a dangerous or abnormal condition of a patient in a hospital as a target condition and automatically sets a detection rule of the target condition. The watching system further automatically detects the patient in the target condition from a video of a camera based on the detection rule.

A hospital is required to be able to find, and quickly cope with, a dangerous or abnormal condition of a patient, thereby preventing deterioration of the condition or preventing it. However, it is difficult to frequently confirm the condition of each patient because of work cost. In such a case, when a detecting system configured to cooperate with a camera and set a dangerous or abnormal condition of a patient as a target condition is introduced, the abnormal condition can be expected to be found at low work cost.

However, the dangerous or abnormal condition may change for each patient. An example is walking. Walking is a normal condition for a general patient. However, walking for a patient who needs absolute rest is an abnormal condition. To cope with such differences between patients, the detection rule of the detecting system needs to be changed depending on the patient.

On the other hand, however, when manually setting the detection rule for each patient, the work cost for the setting of the detection rule becomes high in proportion to the number of patients. In addition, since the condition of a patient changes in accordance with the progress of a symptom or a treatment situation, the detection rule also needs to be reset accordingly. It is therefore necessary to set the detection rule at lower work cost.

As a characteristic feature, the watching system according to this embodiment automatically sets a target condition and a detection rule corresponding to a patient based on patient's medical data to be described later, and detects the target condition based on the automatically set detection rule.

Here, the medical data is, for example, data of a medical chart corresponding to each patient and including personal information such as a name and a face image and at least one piece of medical information such as a symptom or a care instruction. The medical data is not limited to a specific form. For example, the medical data may be a document of a physical medium such as paper or may be digitized.

Examples of medical information are the information of a disease name, a symptom, a morbid portion position, a surgery record, and a care instruction. The form of the medical information is not limited to a specific form. For example, the medical information may be an arbitrary or specific text or may be an attribute expressed as a category or a value. Alternatively, the medical information may be a feature amount or distribution expressed in a specific feature space.

As examples of a use method of the watching system according to this embodiment, for example, a target condition of a hospital patient is detected in a hospital ward, or system cooperation is established between a hospital and a patient's home, and a target condition corresponding to a diagnosis result in the hospital is detected in the home.

First Embodiment

FIG. 1 is a block diagram showing an example of the arrangement of a watching system according to the first embodiment. As shown in FIG. 1, the system includes a detection rule storage device 1, a terminal apparatus 10, a setting apparatus 20, a video supplying device 30, and a detecting apparatus 40. Note that these apparatuses may be connected via a network. As the network, for example, a fixed telephone line network, a portable telephone line network, the Internet, or the like is applicable. In addition, the communication form can be either wired or wireless. These apparatuses may be included in one of the apparatuses.

The detection rule storage device 1 is a storage device configured to store detection rules. As the detection rule storage device 1, a storage device such as a hard disk drive (HDD), a solid state drive (SSD), or an SD memory card can be applied. Note that a plurality of detection rule storage devices 1 may exist and distributively store the detection rules.

The detection rule according to this embodiment is a definition including a processing method for detecting a target condition and the parameters of the processing. Here, the processing method defined by the detection rule includes at least one processing module, the information of the execution order and input/output of the processing modules, and the conditions of detection determination.

Note that as a characteristic feature, the detection rule according to this embodiment includes processing for detecting a target patient. In this embodiment, the definition of processing of detecting a target patient and parameters will particularly be referred to as a person detection rule, and the definition of processing of detecting a target condition and parameters will be referred to as a condition detection rule. In detection, first, a patient in a video is detected based on the person detection rule, and a condition detection rule corresponding to the detected patient is then executed.

The processing method of the person detection rule is not limited to a specific method. For example, a method of collating face images may be used, or a method of reading an ID tag worn by a patient in combination with a sensor may be used. As an example in a case in which a face image is collated, a processing method can be considered in which (1) a face region in a video is detected by face detection processing, (2) a local feature amount is extracted from the image of the detected face region, and (3) detection is performed in a case in which the similarity to the feature amount of a patient registered in advance is equal to or more than a threshold. Additionally, in this case, the feature amount of the patient, the threshold of similarity, and the like can be considered as parameters.

The processing method of the condition detection rule is not limited to a specific method, either. For example, when orientation estimation and motion vector estimation exist as processing modules, a processing method can be considered in which (1) an orientation is estimated from each frame of a video, (2) the coordinates of limbs are extracted from the estimated orientation, (3) a motion vector is estimated for the coordinates of the limbs based on preceding and subsequent frames, and (4) detection is performed in a case in which a motion equal to or more than a threshold is estimated. Additionally, in this case, the size of the search range to estimate the motion vector, the threshold of detection determination, and the like can be considered as parameters.

In addition, an action and condition of a patient, for example, whether a patient is moving a specific part (for example, the right hand) or walking using a cane may be estimated using a CNN (Convolutional Neural Network).

Note that the detection rule may correspond to a single frame of a video or may correspond to a plurality of frames. In addition, the detection rule storage device 1 may store the personal information or the target condition of a patient corresponding to a detection rule in association with the detection rule.

The terminal apparatus 10 is a computer apparatus used by the user of the system, and includes an information presenting unit 11 and an operation detecting unit 12. As the terminal apparatus 10, for example, an information processing apparatus represented by a personal computer (PC), such as a tablet PC, a smartphone, a feature phone, or a smart speaker is applicable. Note that a plurality of terminal apparatuses 10 may exist. In this case, the terminal apparatuses 10 may communicate with each other and share information.

The information presenting unit 11 includes an output device such as an image display panel or a speaker, and presents information input from the setting apparatus 20. The information presenting means is not limited to a specific method. For example, various kinds of user interfaces (UIs) may be displayed on a screen display panel, or information may be converted into a voice and reproduced from a speaker. Note that the UI may be a command UI (CUI) or a graphical UI (GUI).

The operation detecting unit 12 includes an input device such as a controller, a keyboard, a mouse, a touch panel, or a microphone, and detects an operation of the user of the system and also outputs operation information representing the detected operation to the setting apparatus 20. The input device of the operation detecting unit 12 and the output device of the information presenting unit 11 may wholly or partially be shared or connected or may be separated.

The setting apparatus 20 is an apparatus that sets the person detection rule and the condition detection rule of a patient as a target based on medical data input from an external apparatus, and outputs the rules to the detection rule storage device 1. The medical data stored in the external apparatus includes not only a patient ID for identifying each patient and the medical chart (or medical information) of the patient but also information used to identify the face of the patient. Note that when an ID tag is used to identify a patient, a table representing the correspondence relationship between the ID tag and a patient ID is stored in an external storage device.

The setting apparatus 20 includes a condition rule storage unit 26, a condition rule setting unit 21, a data input unit 22, a content analyzing unit 23, a target condition setting unit 24, and a detection rule setting unit 25. The setting apparatus 20 is formed by, for example, an information processing apparatus such as a personal computer, and each processing unit may be implemented by a control program or an application program executed by a CPU.

The condition rule storage unit 26 stores a condition rule (to be described later) input from the condition rule setting unit 21, and outputs it to the target condition setting unit 24. Here, the condition rule is a definition including a processing method for outputting a dangerous or abnormal condition as a target condition based on base information to be described later and the parameters of the processing.

In this embodiment, the target condition is not limited to a specific form. For example, the target condition may be a text such as "moving the right arm" or may be expressed by a combination of an item and one or more values or ranges, for example, "target: right arm, moving amount: 10 or more". In addition, the target condition may be expressed by a point, a set, a range, a distribution, a conditional expression, or the like on a space having one or more coordinate axes corresponding to an item such as a moving amount or an arm angle. Furthermore, the target condition may be selected from a set of candidates of target conditions.

The base information according to this embodiment is information serving as a basis to decide the target condition. The base information is not limited to a specific form. For example, the base information may be an arbitrary or specific text or may be a category or a value representing an attribute. In addition, the base information may be an image or a voice or a combination thereof.

Note that the watching system according to this embodiment uses medical information as base information, and a case in which the base information is medical information will be described below. However, the base information in the embodiment is not limited to medical information.

The form of the condition rule is not limited to a specific form. For example, as an example of the form of a condition rule, the danger level of a condition is defined for each medical information. When medical information and the threshold of the danger level are input, a condition corresponding to a danger level equal to or more than the threshold is output based on the medical information. In this case, it can be considered that, for example, if the medical information is "the right leg is broken", a danger level "80" for "walk without crutches", a danger level "30" for "walk with crutches", and the like are defined. When "50" is designated as the threshold of the danger level, "walk without crutches" is output as the target condition.

As another example of the form of the condition rule, it can be considered that when the information of a damaged part or the degree of damage of a person can be extracted from medical information, a condition in which a load on the damaged part exceeds an allowable range is output as the target condition. In this case, the condition rule defines in advance the allowable range of a load based on the damaged part and the degree of damage. As the processing, for example, pieces of information representing that the damaged part is "right leg", and the degree of damage is "broken" are extracted from medical information such as "the right leg is broken" based on corresponding keywords. After that, a load on the damaged part is calculated for each condition, and if the load exceeds an allowable range defined in advance, the condition is output as the target condition. Note that to calculate the load in each condition, a load defined in advance may be referred to, or a load may be calculated by a physical simulation.

As still another example of the form of the condition rule, it can be considered that information concerning a restriction/prohibition extracted from medical information is extracted, and a condition violating the restriction/prohibition is output as the target condition. In this case, in a case in which, for example, a keyword such as "must not" representing a prohibition is detected from medical information "the patient must not lie face down on the bed when sleeping", a corresponding "condition in which the patient lies face down on the bed when sleeping" is set as the target condition.

As still another example of the form of the condition rule, it can be considered that in a case in which the target condition is expressed on a space having specific coordinate axes, the target condition is output based on an abnormal level generated based on the spatial distance to a "desirable condition" corresponding to medical information. In this case, the "desirable condition" corresponding to the medical information may be defined in advance or may be generated based on a keyword. For example, when the coordinate axes of the space representing a condition correspond to the moving amounts of the parts of a human body, keywords "right arm" and "rest" are extracted from medical information "keep the right arm at rest". As a corresponding "desirable condition", a range in which the value of a coordinate axis corresponding to the moving amount of the right arm becomes equal to or less than a predetermined threshold that can be regarded as a rest is generated. When the desirable condition is decided, a range in which the spatial distance becomes equal to or more than a predetermined threshold is output as the target condition. Note that the parameters of various kinds of thresholds such has the range of the magnitude of a motion that can be regarded as a rest are also defined in advance by the condition rule.

Furthermore, as for the condition rule, the target condition may be output based on a plurality of pieces of medical information. For example, the threshold may be defined not as a constant but as a distribution corresponding to an age. Medical information concerning an age such as "80 years old" may be combined with medical information concerning an exercise restriction such as "vigorous exercises are prohibited", and a condition corresponding to an exercise intensity regarded as a vigorous exercise in a case of 80 years old may be output as the target condition.

In addition, a target condition such as "fall down the stairs" that does not depend on medical information may always be output.

The condition rule setting unit 21 sets (or creates) a condition rule and outputs it to the condition rule storage unit 26. The condition rule storage unit 26 can store a plurality of condition rules. A method of setting the condition rule is not limited to a specific method. For example, a GUI for the setting may be provided to cause the user of the system such as a medical worker to manually define the condition rule, or the condition rule may be defined using an expert system for medical use. Alternatively, the condition rule may be defined using a machine learning method such as Deep Learning based on learning data formed by a set of medical information and a condition of a patient.

Note that the condition rule setting unit 21 sets the condition rule before input of medical data and does not perform individual setting for each medical data. However, there is no limitation for setting the condition rule after input of medical data.

FIG. 2 shows an example in a case in which the condition rule setting unit 21 provides a GUI. FIG. 2 shows a GUI configured to set a condition rule to decide a target condition for each medical information based on the danger level of each condition and a threshold. Reference numeral U21-1 denotes a list of registered medical information. Each row of the list corresponds to medical information, and medical information to be set can be selected by clicking a check box at the left end. Reference numeral U21-2 denotes an input field to register medical information. When an addition button on the right side is clicked in a state in which the text of medical information is input to the text field, the medical information can additionally be registered. Reference numeral U21-3 denotes a list of registered conditions and danger levels. Each row of the list corresponds to each condition, and the danger level of each condition can be input as a numerical value in a danger level input field at the right end. Note that the danger level is independently set for each medical information selected by reference numeral U21-1. Reference numeral U21-4 denotes an input field to register a condition. Here, a condition can additionally be registered, like reference numeral U21-2. Reference numeral U21-5 is a field to input the threshold of a danger level. When a numerical value is input here, the threshold of a danger level as a target condition is set.

A detailed example of setting a condition rule by the user of the system using the GUI shown in FIG. 2 will be described. Here, the condition rule outputs the target condition based on medical information and the threshold of a danger level. First, the user of the system inputs/registers medical information such as "the right leg is broken" or "the left leg is broken" using the text form. Next, a condition such as "walk without crutches", "hit the right leg", or "hit the left leg", is registered like the medical information. After that, the danger level of each condition is input as a value of "0" or more for each medical information. Note that as the danger level of each condition, "0" may be input as an initial value. In addition, the threshold of the danger level of the detection target is input. The condition rule is thus set, which outputs, as a target condition, a condition equal to or more than the threshold of a danger level for each medical information.

However, the GUI of the condition rule setting unit 21 is not limited to the example shown in FIG. 2, and an arbitrary GUI may be used. For example, an image representing a human body may be displayed, and an icon representing a symptom is superimposed on a portion corresponding to a morbid portion, thereby expressing medical information. In addition, in a case in which the target condition is expressed on a space, a slider component corresponding to each coordinate axis of the space may be provided, and the target condition may be defined by operating the slider components.

The data input unit 22 acquires, from an external apparatus, medical data that is the input to the setting apparatus 20, and outputs the medical data to the content analyzing unit 23. The medical data may be acquired from a database such as an electronic medical chart system or a file of a predetermined format such as CSV, or may be acquired by providing a GUI to input medical data. When the GUI is provided, the user of the system may input and confirm the contents using the terminal apparatus 10. Alternatively, instead of receiving medical data from the external apparatus, a physical medium such as paper with medical data may be converted into an image using an input device such as a scanner or a camera, and the medical data may be acquired using a recognition method such as OCR (Optical Character Recognition/Reader). Note that the medical data acquired by the data input unit 22 may be stored by an arbitrary storage unit.

FIG. 3 shows an example in a case in which the data input unit 22 provides an electronic medical chart input GUI. FIG. 3 shows an electronic medical chart GUI capable of inputting the personal information of a patient and a care instruction. Reference numeral U1-1 denotes a text field to input the name of a patient. Reference numerals U1-2 and U1-3 denote pulldown menus to input the sex and age of the patient respectively. Reference numeral U1-4 denotes a text area to input the text of an instruction to a nurse. Reference numeral U1-5 denotes an OK button representing completion of input of the electronic medical chart GUI and a cancel button representing input discard. Reference numeral U1-6 denotes a patient ID used to specify one patient (because there is the possibility of the same name).

However, the GUI of the data input unit 22 is not limited to the example shown in FIG. 3, and an arbitrary GUI can be used. For example, the GUI may include components to input the face image, symptom, and treatment record of the patient. In addition, connection to an external medical information system may be selected on the GUI. A different UI other than the GUI may be used.

Note that the data input unit 22 may include a GUI configured to set a fixed form pattern of partial or whole medical data and enable input of medical data by selecting one or a plurality of fixed form patterns.

The content analyzing unit 23 analyzes medical data input from the data input unit 22 and outputs extracted medical information to the target condition setting unit 24 and the personal information of the patient to the detection rule setting unit 25. As the method of analyzing the medical data, a method using a recognition method such as text recognition such as LSA (Latent Semantic Analysis) or image recognition may be used, or a method of searching for a word corresponding to a predetermined keyword and extracting it may be used.

In addition, an expression such as an abbreviation or an orthographical variant in medical data may be normalized to a unified expression in advance, or a symbol may be converted into a language. For example, when medical information includes a text "Immediately after surgery on the right arm, keep the right arm at rest and take A medicine after meals", examples of medical information to be extracted are "immediately after surgery on the right arm", "keep the right arm at rest", and "take A medicine after meals".

A detailed example of processing performed by the content analyzing unit 23 will be described. Here, assume that medical information candidates are defined in advance in the form of texts such as "the right leg is broken" and "cannot roll over by himself/herself" on the GUI shown in FIG. 2 or the like. At this time, the content analyzing unit 23 applies the LSA to each medical information and extracts the latent meaning of each medical information. Next, the medical data is disassembled into sentences such as "fell down the stairs and broke the right leg", the LSA is applied, and the latent meaning of each sentence of the medical data is extracted. After that, the similarity of latent meanings between the medical information and the medical data is calculated, and medical information having a high similarity to the latent meaning of the medical data is extracted as medical information corresponding to the medical data. For example, when "fell down the stairs and broke the right leg" is given as medical data, medical information such as "the right leg is broken" with a high similarity is extracted.

Upon receiving the medical information from the content analyzing unit 23, the target condition setting unit 24 automatically searches the condition rule storage unit 26 for a condition rule matching the medical information, and outputs the matching condition rule to the detection rule setting unit 25. As the method of setting a target condition, the medical information is input to a processing method defined in each condition rule, and an output condition is set as the target condition. If there exist a plurality of pieces of medical information, each condition output in correspondence with each medical information may be set as a target condition. Note that if no condition is output, a target condition need not be set.

For example, in a case in which the condition rule defines that when medical information and the threshold of a danger level are input, a condition in which the danger level becomes equal to or more than the threshold under the medical information is output, the target condition setting unit 24 inputs medical information and the threshold of the danger level to the condition rule. The threshold of the danger level may be set by providing a GUI that allows the user of the system to do input, or a predetermined value defined in advance may be used. If a plurality of pieces of medical information exist in correspondence with one patient, the condition rule is applied to each medical information to set a plurality of target conditions.

Note that the target condition setting unit 24 may provide a GUI that displays a set target condition and allows the user to select whether to use it as a target condition, and output only a target condition approved by the user of the system. Furthermore, in a case in which a plurality of condition rules exist, a GUI capable of selecting a condition rule to be applied may be provided, and the user of the system may arbitrarily select a condition rule. For example, there may exist a plurality of condition rule sets that are the sets of condition rules such as condition rules for terminal care and condition rules for a surgical ward. A GUI configured to display the outline of each condition rule set and allow the user of the system to select a condition rule set may be provided. In addition, a condition rule to be applied may be selected from a plurality of condition rules based on the medical information.

The detection rule setting unit 25 sets a detection rule based on the personal information of the patient input from the content analyzing unit 23 and the target condition input from the target condition setting unit 24, and outputs the detection rule to the detection rule storage device 1. As a characteristic feature, the detection rule according to this embodiment includes a person detection rule and a condition detection rule. The detection rule setting unit 25 sets a person detection rule corresponding to the personal information and a condition detection rule corresponding to the target condition.

The person detection rule according to this embodiment is set based on the personal information of the patient. However, the processing method of the person detection rule is not limited to a specific form. For example, the face image of the patient prepared in advance may be compared/collated with a face region in a video, or an ID tag worn by the patient may be detected by cooperation with a sensor. In addition, the processing method of the person detection rule may be set individually for each patient, or may be commonly set.

For example, in a case in which the processing method of the person detection rule uses collation of a face image, and is set commonly for all patients, the detection rule setting unit 25 extracts a face image from the personal information of the patient and sets a parameter representing a feature of the face to be used for collation, thereby setting the person detection rule. Note that as the parameter representing the feature of the face, for example, a SIFT feature amount or the like can be used. In this case, the detection processing is performed based on the similarity between a feature amount extracted from a video and a feature amount extracted in advance.

The condition detection rule setting method according to this embodiment is not limited to a specific method. For example, every time a target condition is input, an appropriate condition detection rule may be estimated. Alternatively, a condition detection rule corresponding to each target condition may be set in advance, and a condition detection rule corresponding to an input target condition may be referred to. In addition, the condition detection rule may automatically be set by the system, or may manually be set by the user of the system. Furthermore, these may be combined.

As an example of the condition detection rule setting method, in a case in which, for example, the target condition is expressed by a combination of one or more attributes such as "part: right arm, moving amount: 10 or more", a method of setting processing corresponding to each attribute and thus setting a condition detection rule is usable. In the case of this example, the target condition is defined by the attributes of a human body part and a moving amount. For example, it is possible to automatically set orientation estimation processing as processing corresponding to the part attribute and motion vector estimation processing as processing corresponding to the moving amount attribute. When the condition detection rule is thus set, detection processing of performing detection when the moving amount of the right arm portion is 10 or more can be executed.

Additionally, for example, in a case in which the target condition is expressed by a specific feature amount, processing of extracting a corresponding feature amount and processing of obtaining a similarity by comparing the extracted feature amount with the target condition are set, thereby automatically setting the condition detection rule.

Figure 4:
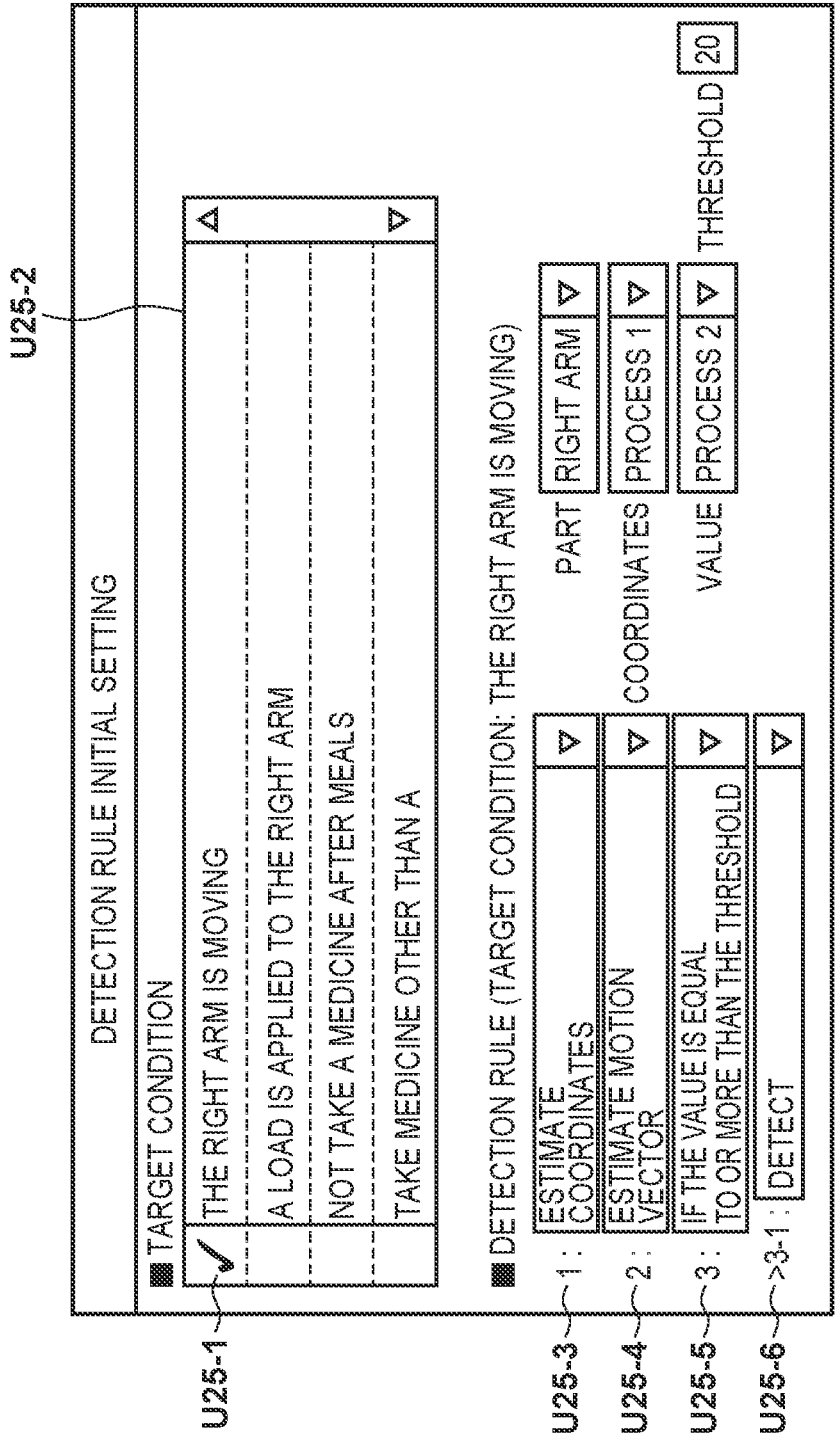
FIG. 4 is a view showing an example of the GUI of a detection rule setting unit according to the first embodiment.

As an example of the method of manually setting the condition detection rule, a method of setting a condition detection rule corresponding to each target condition by a GUI can be used. FIG. 4 shows an example of a GUI provide by the detection rule setting unit 25 in this case. FIG. 4 shows a GUI that causes the user of the system to set a condition detection rule corresponding to each target condition. Reference numerals U25-1 and U25-2 denote tables showing target conditions, and each row corresponds to a target condition. Reference numeral U25-1 denotes a column of checkboxes configured to select a target to set a condition detection rule. In reference numeral U25-1, one or a plurality of target conditions can be selected. In a case of selecting a plurality of target conditions, a common condition detection rule is set for the selected target conditions. Reference numeral U25-2 denotes a column to display texts representing the target conditions. Reference numerals U25-3 to U25-6 denote pulldown menus and text fields used to set a condition detection rule. Reference numerals U25-3 to U25-6 correspond to the processes and parameters of a condition detection rule, and they are executed in order. However, if the processes are independent, they may be executed in random order or in parallel. Note that the parameter of each processing changes in accordance with the selected processing. The parameter U25-3 represents coordinate estimation processing of a human body part. As the parameter of the target part, the right arm is set. The parameter U25-4 represents motion vector estimation processing. Here, as the parameters of target coordinates, the processing result of the parameter U25-3, that is, the estimated coordinates of the right arm are set. The parameter U25-5 represents processing of condition branching in a case in which an input value is equal to or more than a threshold. The output of the parameter U25-4, that is, the motion vector of the right arm portion is set as the parameter of the input value, and "20" is set as the parameter of the threshold. The parameter U25-6 is executed only in a case in which the conditions defined by the parameter U25-5 are satisfied, and represents that detection processing is performed. These processes can be changed by selecting the processes or the parameters from the pulldown menus and text fields. However, the GUI used to set the condition detection rule is not limited to the example shown in FIG. 4, and an arbitrary GUI may be used. For example, a component configured to visualize a target condition by an image or a video and display it may be included. In addition, a button component configured to add or delete a processing step may be included.

A detailed example of setting the condition detection rule of a target condition using the GUI shown in FIG. 4 will be described. Here, assume that the condition detection rule is independently set for each target condition, and an arbitrary number of processing steps are executed in order. First, the user of the system selects a target condition to set a condition detection rule on the GUI. Next, each process to be executed by the condition detection rule is set for each processing step. Candidates of processes executable in each processing step are defined on the system in advance. The user of the system selects a process candidate and inputs a parameter. For example, for a target condition "walk without crutches", a condition detection rule shown below is set. This condition detection rule defines processes and parameters to detect the target condition when walking is detected by action recognition, and crutches are not detected by object detection.

(1) Process [action recognition], parameter [(target action) walk]

(2) Process [object detection], parameter [(object) crutches]

(3) Process [condition branching], parameter [(condition) process 1 for detection success, and process 2 for detection failure]

(3-1) Process [detection notification]

Here, the process of condition branching indicates processing of executing the next processing step only in a case in which the condition is satisfied, and interrupting the processing in a case in which the condition is not satisfied. In addition, the process of detection notification is processing of outputting, to the system, information representing that the target condition is detected. Note that the processes have different parameters. When the user of the system selects a process, an input field of the corresponding parameter is displayed on the GUI.

Note that in a case in which the condition detection rule corresponding to the target condition cannot be set by the detection rule setting unit 25, a message representing that the setting of the detection rule has failed may be displayed on the information presenting unit 11 of the terminal apparatus 10 or the like, thereby notifying the user of the system of it.

The video supplying device 30 is a device configured to acquire a video and output the acquired video to the detecting apparatus 40. The video supplying device 30 and the detecting apparatus 40 are connected via a network for communication. The communication form can be either wired or wireless. The video supplying device 30 may include an image capturing device such as a network camera, a web camera, or a wearable camera and acquire and output a video of the environment in which the device is installed, or may include a storage device such as an HDD or an SSD and output a stored video. In addition, when acquiring a video, the video supplying device 30 may acquire the information of the image capturing environment such as the place where the video is captured and the angle of field and output the information in association with the video. In addition, a plurality of video supplying devices 30 may exist, and a plurality of videos may be output to the detecting apparatus 40.

The detecting apparatus 40 is an apparatus configured to detect the target condition corresponding to the patient based on the detection rule and notify the detection result. The detecting apparatus 40 includes a video acquiring unit 41, a detection determining unit 42, and a detection result presenting unit 43 shown in FIG. 1.

The video acquiring unit 41 acquires a video from the video supplying device 30, and outputs it to the detection determining unit 42. The detection determining unit 42 performs detection processing based on the video input from the video acquiring unit 41 and a detection rule referred to from the detection rule storage device 1, and outputs a detection result to the detection result presenting unit 43.

The detection determining unit 42 first executes the processing of the person detection rule and detects that a registered patient is included in the video. If the registered patient is detected, processing of the condition detection rule corresponding to the patient is executed. After that, a target condition detected as the detection result is output to the detection result presenting unit 43. However, if a registered patient or target condition is not detected, information representing that nothing is detected is output as the detection result.

The detection result presenting unit 43 provides a GUI configured to visualize the detection result input from the detection determining unit 42 and displays it on the information presenting unit 11 of the terminal apparatus 10, thereby presenting the detection result to the user of the system. As for the contents to be displayed, not only the presence/absence of detection but also a plurality of pieces of associated information such as information concerning the target condition and the instruction of an action that the user of the system should make may be presented. In addition, the detection result may be converted into a voice and presented by a speaker or the like. The detection result presenting unit 43 may further include a GUI configured to do settings of the detection result presenting method and contents such that the user of the system can set the presenting method and contents.

Figure 5:
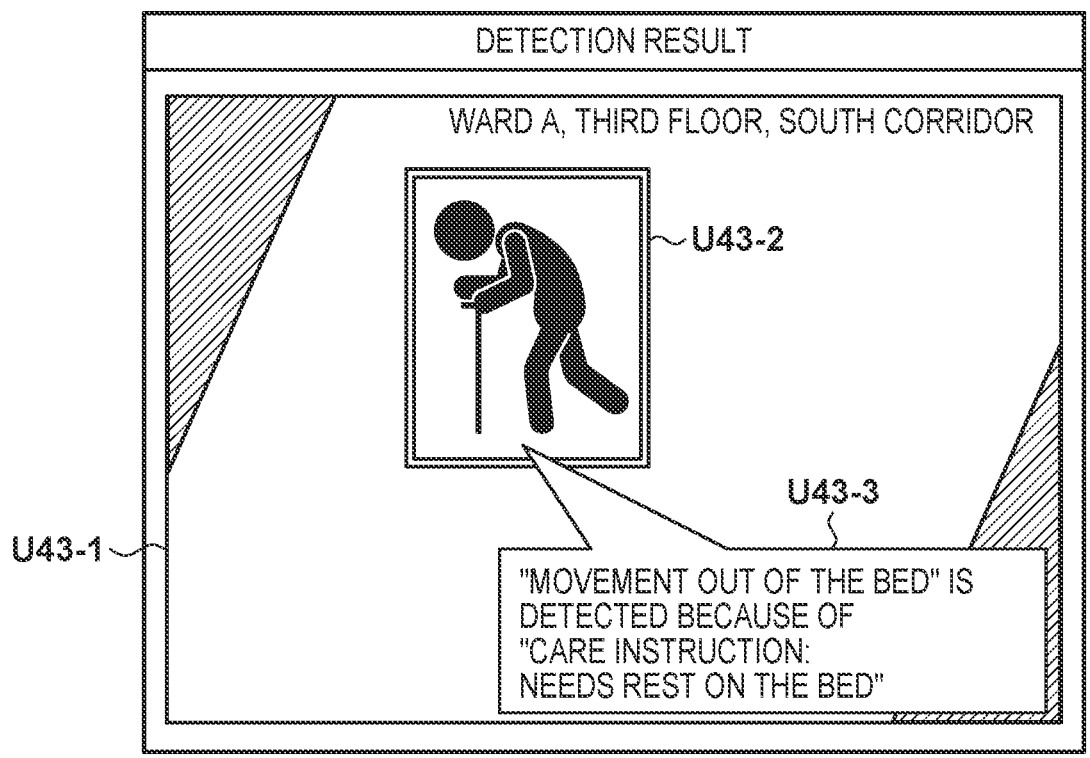
FIG. 5 is a view showing an example of the GUI of a detection result presenting unit according to the first embodiment.

FIG. 5 shows an example of the GUI provided by the detection result presenting unit 43. FIG. 5 shows a GUI configured to superimpose the information of a detection result on a video at the time of detection. Reference numeral U43-1 denotes a window that displays the video or image at the time of detection. When the window U43-1 displays the captured video, buttons such as play and pause buttons used to control the video may be provided and displayed. Reference numeral U43-2 denotes a frame indicating a portion in the video or image corresponding to the detection result. When the window U43-1 displays the video, the frame U43-2 also deforms and moves along with a change of the video. Reference numeral U43-3 denotes a popup component that displays details of the detection result. Examples of contents displayed by the popup component U43-3 are a position in medical data corresponding to the detection result, the target condition, and the detection rule.

Note that although FIG. 1 shows the setting apparatus 20, the detection rule storage device 1, and the detecting apparatus 40 as separate apparatuses, these may be implemented by one apparatus. In addition, the apparatus may include the terminal apparatus 10.

Figure 6:
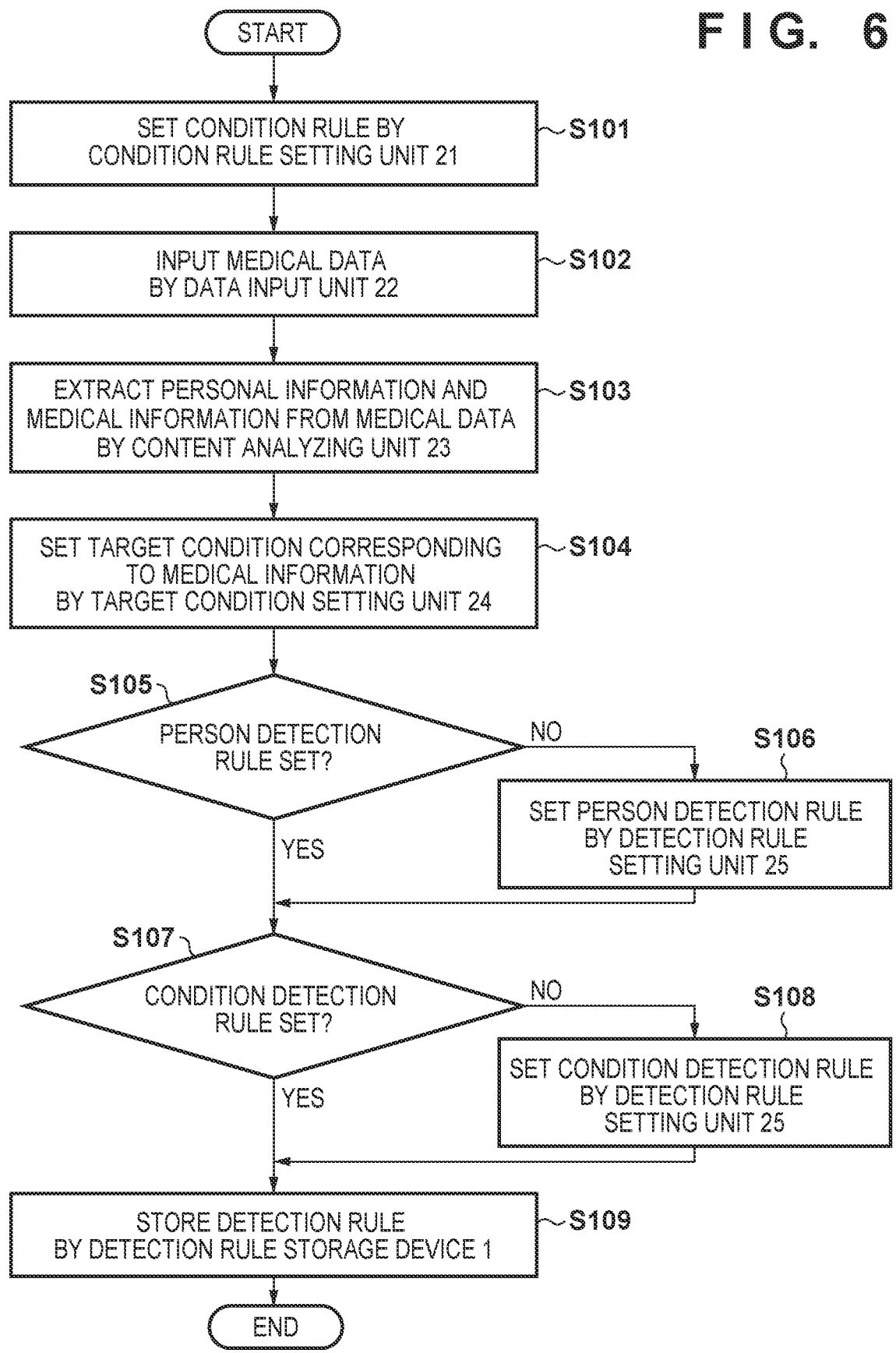
FIG. 6 is a flowchart showing an example of a detection rule setting procedure according to the first embodiment.

FIG. 6 is a flowchart showing an example of a detection rule setting procedure according to the first embodiment. The detection rule setting procedure according to the first embodiment will be described below with reference to FIG. 6.

1. The condition rule setting unit 21 sets a condition rule. This processing corresponds to step S101 in FIG. 6.

2. The data input unit 22 inputs medical data of a patient. This processing corresponds to step S102 in FIG. 6.

3. The content analyzing unit 23 analyzes the contents of the medical data and extracts personal information and medical information. This processing corresponds to step S103 in FIG. 6.

4. The target condition setting unit 24 sets a target condition based on the condition rule and the medical information. This processing corresponds to step S104 in FIG. 6.

5. If the detection rule storage device 1 does not store a person detection rule corresponding to the personal information, the detection rule setting unit 25 sets a person detection rule. This processing corresponds to steps S105 and S106 in FIG. 6.

6. If the detection rule storage device 1 does not store a condition detection rule corresponding to the target condition, the detection rule setting unit 25 newly sets a condition detection rule. This processing corresponds to steps S107 and S108 in FIG. 6.

7. The detection rule storage device 1 stores the person detection rule and the condition detection rule corresponding to the patient. This processing corresponds to step S109 in FIG. 6.

With the above-described processing, a detection rule corresponding to the medical data of the patient can be set. However, the processing procedure according to this embodiment is not limited to that described above. For example, candidates of condition detection rules may be set in advance before the medical data is input.

Figure 7:
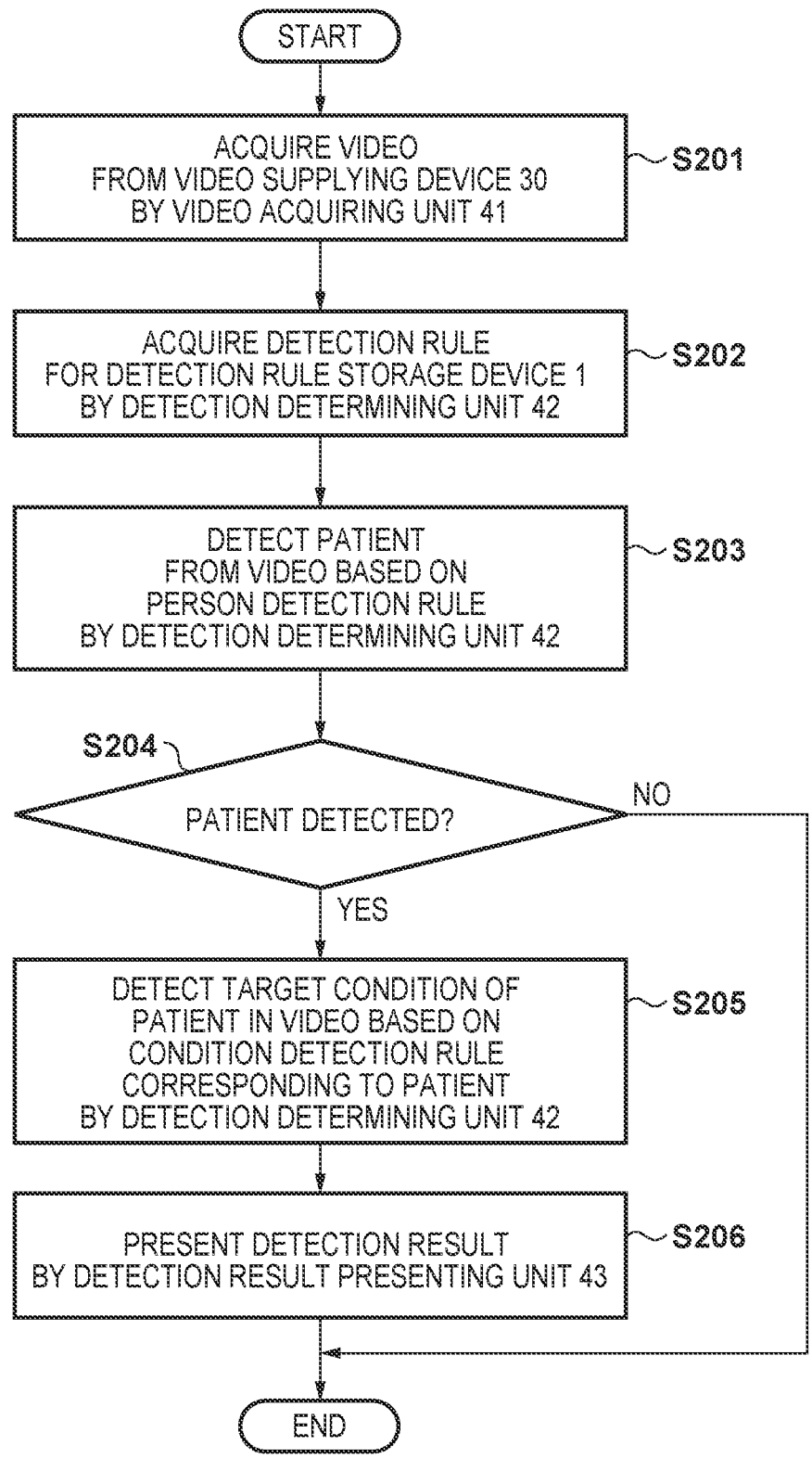
FIG. 7 is a flowchart showing an example of a detection procedure according to the first embodiment.

FIG. 7 is a flowchart showing an example of a detection procedure according to this embodiment. The processing procedure will be described below with reference to FIG. 7.

1. The video acquiring unit 41 acquires a video from the video supplying device 30. This processing corresponds to step S201 in FIG. 7.

2. The detection determining unit 42 acquires a detection rule from the detection rule storage device 1. This processing corresponds to step S202 in FIG. 7.

3. The detection determining unit 42 detects a patient from the video based on the person detection rule and identifies the patient. This processing corresponds to step S203 in FIG. 7.

4. If no patient is detected, the processing is ended. This processing corresponds to step S204 in FIG. 7.

5. The detection determining unit 42 detects the target condition of the patient in the video based on a condition detection rule corresponding to the patient. This processing corresponds to step S205 in FIG. 7.

6. The detection result presenting unit 43 presents the detection result to the user of the system. This processing corresponds to step S206 in FIG. 7.

As described above, according to the first embodiment, it is possible to set a detection rule based on medical data and detect a target condition from a video. However, the detection rule setting method and the detection method described here are merely examples and are not limited to these examples.

Figure 14:
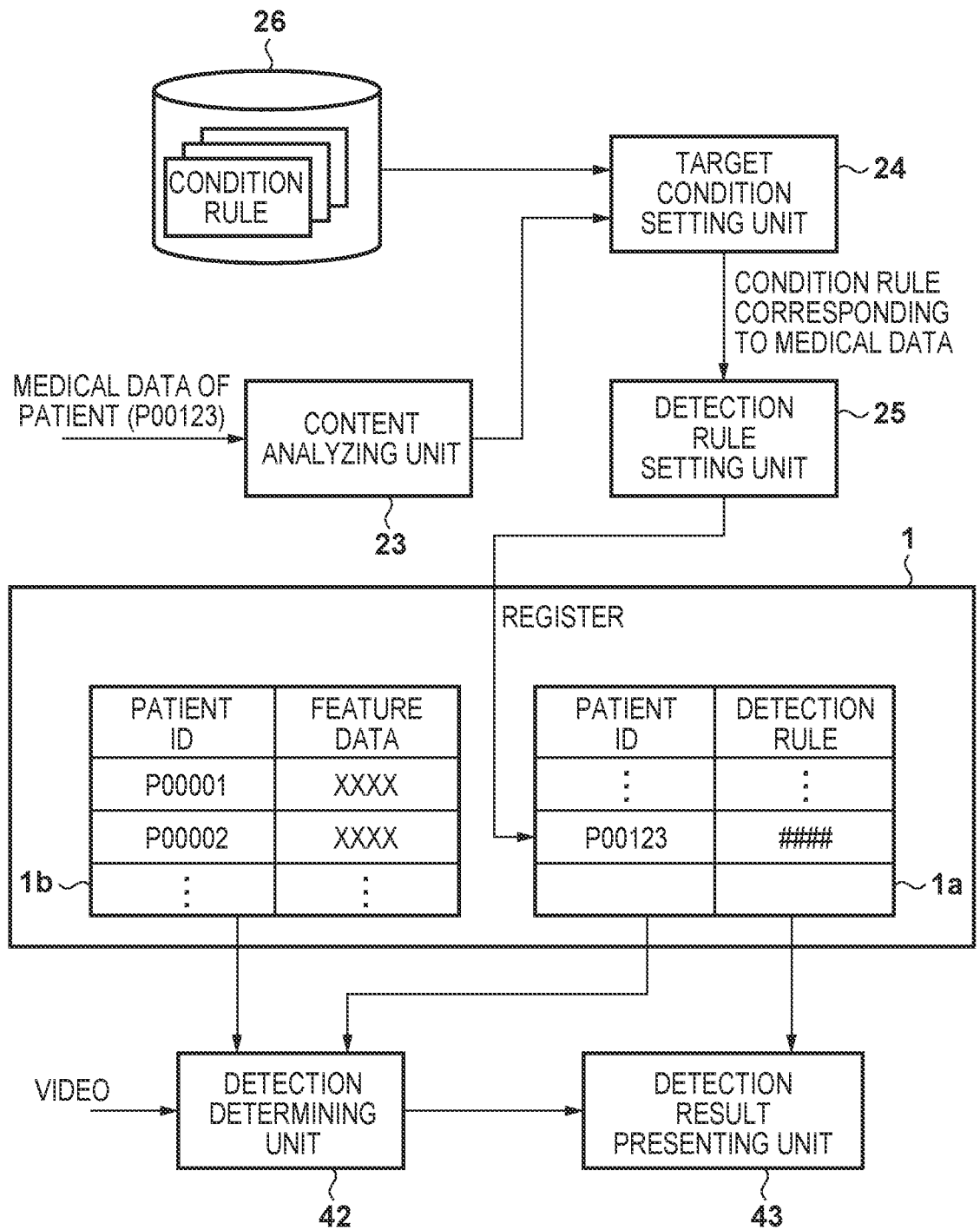
FIG. 14 is a view for explaining the outline of a movement according to the fourth embodiment.

For easier understanding of the movement according to the first embodiment, a description will be made again with reference to FIG. 14. Note that although FIG. 14 corresponds to FIG. 1, several components are not illustrated for the sake of simplicity.

The condition rule storage unit 26 stores a plurality of pieces of rule information each defining a condition (for example, a disease name such as right leg fracture) of an object and a movement (for example, walk without crutches) that derives from the condition and should be observed concerning the object (FIG. 2).

Assume that the content analyzing unit 23 newly receives information (medical data of patient ID: P00123) representing the condition of a monitored object. The content analyzing unit 23 analyzes the medical data and detects a result (a patient ID and a disease name). The target condition setting unit 24 receives the analysis result, and acquires rule information matching the condition obtained by the analysis from a number of condition rules registered in the condition rule storage unit 26. Based on the information from the target condition setting unit 24, the detection rule setting unit 25 registers, in a detection rule database 1a of the detection rule storage device 1, information that defines a movement to be observed for the monitored object (here, patient ID: P00123).

Assume that the video acquiring unit 41 receives a video of an object (a person walking in the hospital) from a certain video supplying device 30. Note that at this stage, whether the object (person) in the video is a patient does not matter. The detection determining unit 42 extracts feature information from the object and compares it with feature information registered in a monitored object database (patient database) 1b in the detection rule storage device 1, thereby determining whether the object in the video is a monitored object (one of registered patients). If the object in the video is a non-monitored object, processing is not performed anymore. If it is found that the object in the video is a monitored object, the detection determining unit 42 determines that the object in the video to be input from then on is the monitored object, and starts monitoring (tracking) of its movement. During monitoring processing, the detection determining unit 42 determines whether the condition (the patient of the patient ID: P00123 walks without crutches, or the right leg hits an object) to be observed for the monitored object in the detection rule database 1a is obtained, and supplies the determination result to the detection result presenting unit 43. Based on this information, in a case in which the monitored object performs the movement to be observed (in a case in which one of walking of the patient of the patient ID: P00123 without crutches and hit of the right leg against an object is detected), the detection result presenting unit 43 determines this as abnormality, and presents the detection result to the user of the system.

As a result, in a case in which the information representing the condition of the monitored object is received, it is possible to automatically decide rule information representing a movement to be observed in correspondence with the condition without performing a specific operation or setting of the object. In addition, it is possible to monitor, for each monitoring target, whether there is a movement to be observed, which is unique to the monitoring target.

Second Embodiment

In the first embodiment, an in-hospital watching system configured to set a detection rule corresponding to a patient has been described. In the second embodiment, a case in which processing is added to the in-hospital watching system according to the first embodiment to automatically update the detection rule in accordance with updating of medical data will be described. A case in which the user of the system corrects an automatically set target condition or detection rule will also be described.

In the hospital, the target condition to be detected sometimes changes due to a change in the treatment situation or symptom of a patient. For example, for a patient who needs absolute rest, a condition in which the patient walks about in the hospital is the target condition. However, the detection becomes unnecessary when the patient recovers and is permitted to walk about in the hospital. At this time, if the detection rule is automatically updated in accordance with updating of the medical data, the detection rule need not be reset explicitly. It is therefore possible to reduce the work man-hour.

The watching system according to the second embodiment includes an arrangement common to the watching system according to the first embodiment. Hence, in the second embodiment, portions different from the first embodiment will be described.

Figure 8:
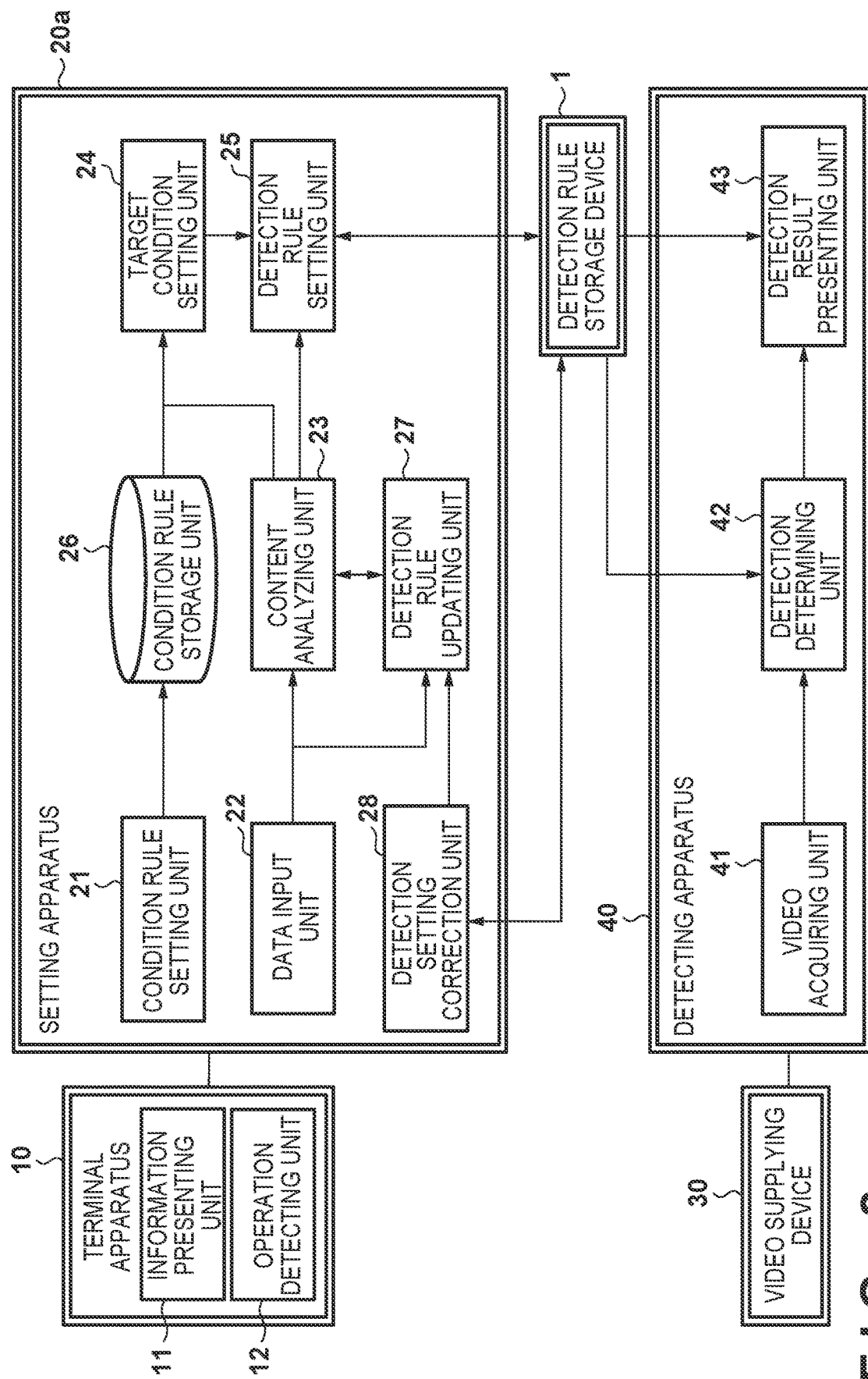
FIG. 8 is a block diagram of the arrangement of a watching system according to the second embodiment.

FIG. 8 is a block diagram showing an example of the arrangement of the watching system according to the second embodiment. As shown in FIG. 8, the watching system according to the second embodiment includes a detection rule storage device 1, a terminal apparatus 10, a setting apparatus 20a, a video supplying device 30, and a detecting apparatus 40. Note that these apparatuses may be connected via a network. As the network, for example, a fixed telephone line network, a portable telephone line network, the Internet, or the like is applicable. In addition, these apparatuses may be included in one of the apparatuses.

The setting apparatus 20a is an apparatus that sets a target condition and a detection rule based on medical data input from the outside, and outputs them to the detection rule storage device 1, like the setting apparatus 20 according to the first embodiment. As a characteristic feature, the setting apparatus 20a includes a condition rule storage unit 26, a condition rule setting unit 21, a data input unit 22, a content analyzing unit 23, a target condition setting unit 24, and a detection rule setting unit 25, like the setting apparatus 20 according to the first embodiment, and also includes a detection rule updating unit 27 and a detection setting correction unit 28, as shown in FIG. 8.

The detection setting correction unit 28 provides a GUI configured to cause the user of the system to confirm and correct contents set by the components of the setting apparatus 20a, and replaces a detection rule stored in the detection rule storage device 1 with a corrected detection rule. Targets to be corrected by the setting apparatus 20a are medical information extracted by the content analyzing unit 23, a target condition set by the target condition setting unit 24, and a detection rule set by the detection rule setting unit 25. The detection setting correction unit 28 may provide a GUI capable of correcting all of them, or may provide a GUI configured to correct some of them.

Figure 9:
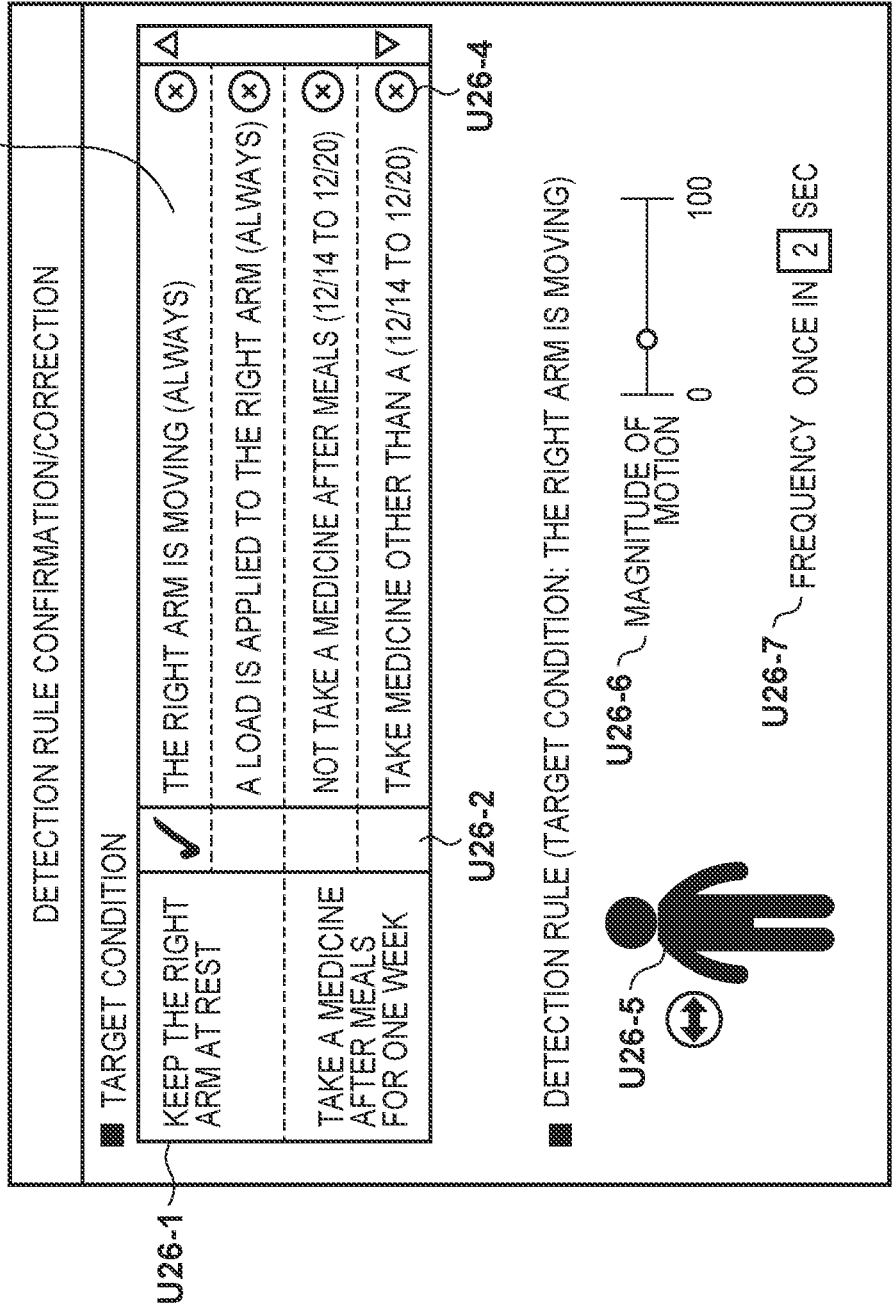
FIG. 9 is a view showing an example of the GUI of a detection setting correction unit according to the second embodiment.

As an example of the GUI provided by the detection setting correction unit 28, for example, a GUI as shown in FIG. 9 can be used. FIG. 9 shows a GUI that displays a target condition and a detection rule and allows the user of the system to correct them. Reference numerals U26-1 to U26-4 denote items capable of displaying and selecting target conditions, and each row corresponds to a target condition. The item U26-1 shows medical information used to set a detection rule. The item U26-2 is a column of checkboxes to select a target condition. The item U26-3 is a region to display a target condition. A period for each target condition is also displayed in the region U26-3, and a target condition in a corresponding period is a target of detection. Note that the period of each target condition is set based on the detection rule updating unit 27 to be described later. When the period of a target condition is selected by double-click or the like, an editing condition is set, and the period can be corrected. The button U26-4 is prepared to delete each target condition. When the button U26-4 is clicked, the target condition and the corresponding detection rule are deleted. Reference numeral U26-5 denotes an image or a video representing an example of a target to be detected by a detection rule. For example, this is an image representing a human body or an icon showing a condition such as a movement. This icon may be superimposed to show the condition of a corresponding part at the position of the icon. In addition, an animation showing a condition of detection may be reproduced. Reference numerals U26-6 and 26-7 denote a slider and a text field used to adjust the parameters of the detection rule corresponding to the selected target condition. The type of the parameter settable her changes depending on the type of the parameter included in the detection rule. In addition, when the parameter of the detection rule is corrected, the detected condition represented by the slider U26-6 also changes in synchronism. The slider U26-6 is a slider configured to set the threshold of the magnitude of the movement to be detected. The frequency of detection is set in the text field U26-7. By the text field, the interval of time to execute detection processing can be set.

Note that in a case in which a detection setting is changed by the user of the system, the detection setting correction unit 28 may correct the behavior of each component of the setting apparatus 20a. For example, if a target condition "the right arm is moving" corresponding to medical information "keep the right arm at rest" is deleted, the corresponding condition rule may be corrected and thus changed so the same target condition is not set after that. In addition, when the parameter of a detection rule is corrected, changing may be performed so as to set the detection rule of the corrected parameter for the same target condition after that.

The detection rule updating unit 27 updates (resets) the detection rule based on the medical data input from the data input unit 22, the medical information input from the content analyzing unit 23, and the like. The timing (to be referred to as an updating timing hereinafter) of updating the detection rule is decided by some or all of methods to be described below.

As one of the methods of deciding the updating timing, there is a method of performing updating when updating of medical data is detected. In this case, since the detection rule is set based on the latest medical data, it is possible to quickly cope with a change in medical information.

The method of detecting updating of medical data is not limited to a specific method. For example, the updating date/time of medical data may be stored, and updating may be detected in a case in which the latest updating date/time is newer than the stored date/time. Alternatively, medical data may be input to the content analyzing unit 23, and updating may be detected in a case in which output medical information changes.

As another method of deciding the updating timing, there exists a method of extracting the information of a period such as the date/time of start or the date/time of end from medical information and making the updating timing match the start and end of the period. For example, in a case in which medical information "absolute rest for two days" is input, the detection rule is updated using medical information other than "absolute rest" two days after the date/time of input of the medical information.

Additionally, even in a case in which an explicit period is not designated, the period may be estimated based on the medical information concerning the symptom or treatment method. The period corresponding to the symptom or medical method may be set manually in advance, or may be estimated by referring to a database concerning a general treatment period of the symptom. For example, in a case in which there is medical information "infected by influenza", and a setting "the treatment period of influenza is about one week" is manually done, the detection rule is updated based on medical information other than "infected by influenza" at a timing after the elapse of one week.

When the detection rule updating unit 27 detects updating of medical data, the updated medical information is output to the content analyzing unit 23. If the medical information is changed, the content analyzing unit 23 outputs the changed medical information to the target condition setting unit 24. The target condition setting unit 24 sets a target condition based on the changed medical information. In a case in which the target condition changes as compared to that before the medical information changes, or the target condition changes by a predetermined amount or more, the target condition is output to the detection rule setting unit 25. The detection rule setting unit 25 resets the detection rule and outputs it to the detection rule storage device 1. The detection rule storage device 1 replaces the past detection rule with the reset detection rule and stores it.

If the detection rule is reset along with the updating of the medical information, the detection rule updating unit 27 may present the detection rule changed by the resetting to the user of the system by a GUI or the like. In addition, the user of the system may be confirmed about whether to approve the resetting of the detection rule, and the detection rule may be replaced only when the updating is approved.

In the above-described way, it is possible to detect updating of medical data and reset the detection rule. In addition, the user of the system can confirm and reset the detection rule. However, the example described in this embodiment is merely an example and is not limited.

Third Embodiment

In the third embodiment, a case in which processing is added to the watching system according to the first embodiment to adjust a detection rule in accordance with the image capturing environment of a video will be described.

In a detecting system that handles videos of a plurality of cameras, the image capturing conditions of the videos may be different. Here, the image capturing conditions are various kinds of conditions including the position and orientation of a camera, parameters of a camera such as a frame rate, and environmental conditions such as illumination. At this time, even in a case in which the same target condition should be detected, the detection rule is sometimes preferably changed for each video.

For example, assume that a detection rule that defines performing motion vector estimation and performing detection based on the magnitude of a moving amount is set. In this case, if the frame rate of a video changes, the amount of the estimated motion vector also changes. Hence, it is difficult to perform appropriate detection.

As a characteristic feature, the watching system according to the third embodiment changes a detection rule in correspondence with the image capturing conditions of a video, thereby performing detection processing suitable for each video.

Figure 10:
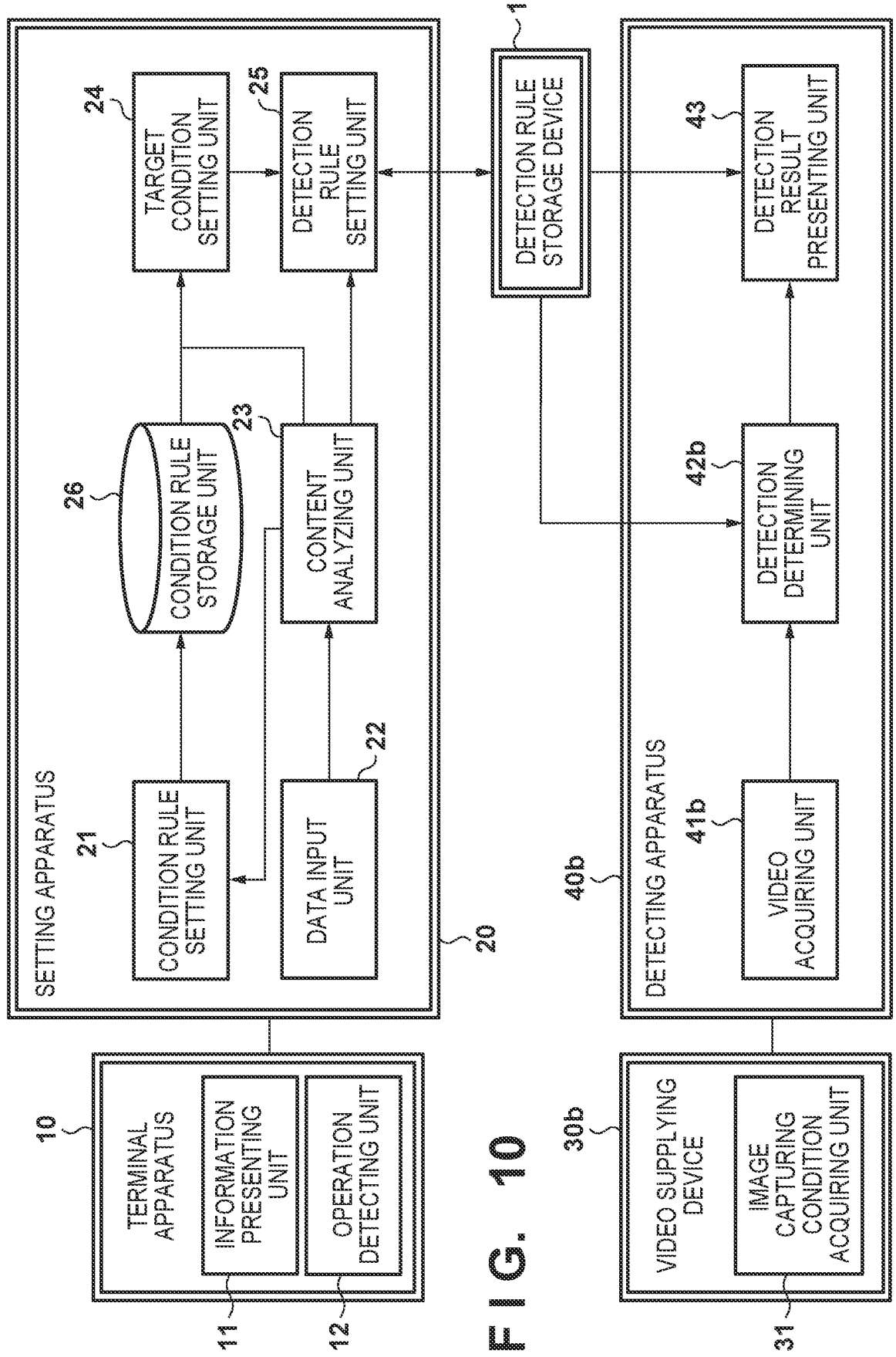
FIG. 10 is a block diagram showing an example of the arrangement of a watching system according to the third embodiment.

The watching system according to the third embodiment includes an arrangement common to the watching system according to the first embodiment. Hence, in the third embodiment, portions different from the first embodiment will be described. FIG. 10 is a block diagram showing an example of the arrangement of the watching system according to the third embodiment. As shown in FIG. 10, the work management system according to the third embodiment includes a detection rule storage device 1, a terminal apparatus 10, a setting apparatus 20, a video supplying device 30b, and a detecting apparatus 40b. Note that these apparatuses may be connected via a network. As the network, for example, a fixed telephone line network, a portable telephone line network, the Internet, or the like is applicable. In addition, these apparatuses may be included in one of the apparatuses.

The video supplying device 30b is a device configured to acquire a video and output the acquired video to the detecting apparatus 40b, like the video supplying device 30 according to the first embodiment. The video supplying device 30b includes an image capturing condition acquiring unit 31 in addition to the function of the video supplying device 30 according to the first embodiment. The image capturing condition acquiring unit 31 acquires an image capturing condition for each video supplied by the video supplying device 30b and outputs the image capturing condition to a video acquiring unit 41b of the detecting apparatus 40b.

The method of acquiring the image capturing condition is not limited to a specific method. For example, in a case in which the video supplying device 30b includes a camera device and acquires a video from the camera device, a method of accessing the camera device to acquire image capturing parameters such as a frame rate and a resolution can be used. In addition, in a case in which the video supplying device 30b acquires video file data, a method of acquiring an attribute concerning the image capturing condition from the information of the attribute included in the video file data can be used. In addition, the image capturing condition acquiring unit 31 may provide a GUI used to input an image capturing condition for each video and cause the user of the system to directly input the image capturing condition to acquire the image capturing condition.

The detecting apparatus 40b is an apparatus configured to detect a target condition based on a detection rule and notify the detection result, like the detecting apparatus 40 according to the first embodiment. The detecting apparatus 40b includes a detection result presenting unit 43 shown in FIG. 10 and also includes a video acquiring unit 41b and a detection determining unit 42b.

The video acquiring unit 41b acquires a video and an image capturing condition from the video supplying device 30, and outputs them to the detection determining unit 42b, like the video acquiring unit 41 according to the first embodiment.

The detection determining unit 42b performs detection processing based on the video and the image capturing condition input from the video acquiring unit 41b and the detection rule referred to from the detection rule storage device 1, and outputs the detection result to the detection result presenting unit 43. As a characteristic feature, the detection determining unit 42b changes the detection rule in correspondence with the image capturing condition. However, the method of changing the detection rule is not limited to a specific method.

As an example of the method of changing the detection rule by the detection determining unit 42b, a method of changing input/output of a specific process in the detection rule in correspondence with the image capturing condition can be used. For example, in a case in which "motion vector estimation processing" is executed by the detection rule, a method of dividing the motion vector amount to be output by the frame rate is used. As the characteristic of motion vector estimation processing, the estimation amount of the motion vector is reversely proportional to the frame rate. Hence, the motion vector amount can be normalized with respect to the frame rate by dividing it by the frame rate. In addition, for example, processing of converting the resolution of a video into a predetermined size may be added.

In the above-described way, even if the image capturing condition changes between videos, appropriate detection processing can be executed by automatically changing the detection rule. That is, it is possible to perform detection processing based on one detection rule for videos from an unspecified number of video supplying devices with different image capturing conditions.

Fourth Embodiment

The fourth embodiment will be described. In the fourth embodiment, a case in which a dangerous or abnormal condition of a worker or a machine is detected from a video of a camera based on a detection rule automatically set in correspondence with a work in a factory will be described as an example.

In a factory, there is a demand to be able to find a dangerous or abnormal condition of a worker or a machine and quickly cope with it, thereby preventing an occurrence of an accident or a defective product. However, it is difficult to frequently confirm the state of a work because of work cost. In this case, a detecting system that cooperates with a camera is introduced, and a dangerous or abnormal condition of a worker or a machine is set as a target condition, so that the condition can be expected to be automatically detected.

A dangerous or abnormal condition in the factory can be detected by the same arrangement and processing as the watching system described in the first embodiment. However, the work management system according to this embodiment is different from the watching system according to the first embodiment in the following points.

First, to set a detection rule, not medical data but a work instruction data to be described later is used. Next, the detection rule is set not for each patient but for each work performed by a worker. Furthermore, a condition rule can automatically be added based on the work instruction data to be described later.

The work instruction data according to the fourth embodiment is data of an incident report or a work standard document including work instruction information that is the information of an instruction concerning a work method. Examples of the work instruction information is a work category such as "roller assembling", a work order, a note for each work such as "measure an assembling position by a scale", and the information of a qualification needed for each work. Note that the work instruction data or work instruction information is not limited to a specific form and can be an arbitrary form, like the medical data or medical information according to the first embodiment.

FIG. 11 shows an example of work instruction data. FIG. 11 shows an example of a work standard document to attach a sack to a tube and charge a powder. A field WS-1 stores information representing the order of works. A field WS-2 stores information representing detailed work contents such as "place a box under a tube" and "inject a powder". A field WS-3 stores the information of remarks such as a note for each work, for example, "remove static electricity in advance". The field WS-3 may have no information described depending on the work.

FIG. 12 shows another example of work instruction data. FIG. 12 shows an example of a report of an incident that has occurred during a powder charging work. Reference numeral HR-1 denotes a date/time of the occurrence of an incident; HR-2, a work performed at the time of the incident;

and HR-3, contents of the incident. Reference numeral HR-4 denotes a cause of the incident; HR-5, a measure to prevent the occurrence of the incident; and HR-6, a photo of the site where the incident has occurred in which an arrow indicates a point that is the cause of the incident.

Concerning the watching system according to the first embodiment, a case in which a condition rule is set in advance, thereby setting a target condition corresponding to medical data has been described. However, since the relationship between a work and a target condition is not necessary obvious, it is sometimes difficult to set a comprehensive condition rule in advance. As a characteristic feature, the work management system according to the fourth embodiment extracts a target condition corresponding to a work from work instruction data and adds a condition rule.

The work management system according to the fourth embodiment includes an arrangement common to the watching system according to the first embodiment. Hence, in the fourth embodiment, portions different from the first embodiment will be described.

Figure 13:
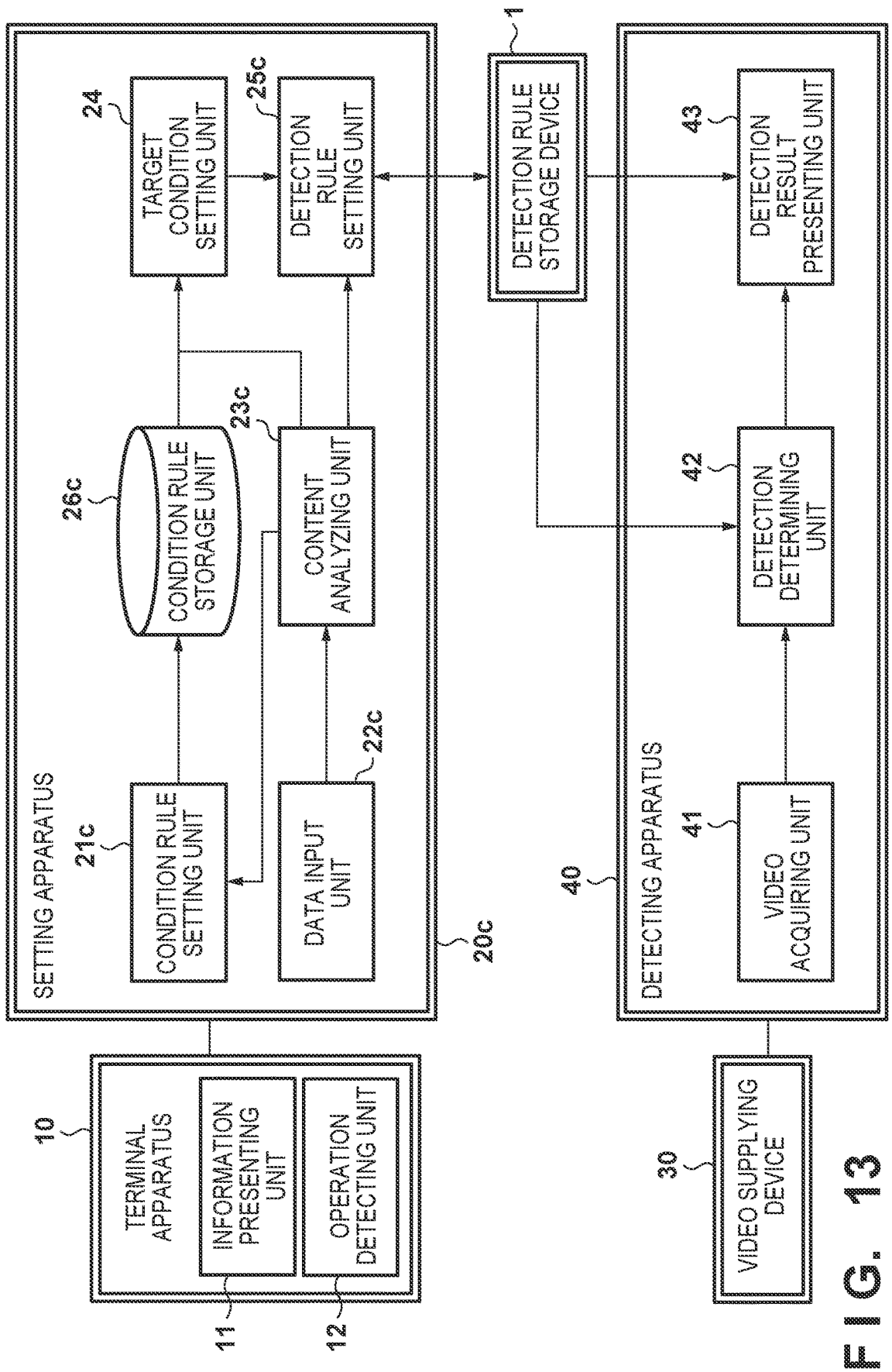
FIG. 13 is a block diagram showing an example of the arrangement of a work management system according to the fourth embodiment.

FIG. 13 is a block diagram showing an example of the arrangement of the work management system according to the fourth embodiment. As shown in FIG. 13, the work management system according to the fourth embodiment includes a detection rule storage device 1, a terminal apparatus 10, a setting apparatus 20c, a video supplying device 30, and a detecting apparatus 40. Note that these apparatuses may be connected via a network. As the network, for example, a fixed telephone line network, a portable telephone line network, the Internet, or the like is applicable. In addition, these apparatuses may be included in one of the apparatuses.

The setting apparatus 20c is an apparatus that sets a target condition and a detection rule corresponding to work instruction information based on work instruction data, and outputs them to the detection rule storage device 1, like the setting apparatus 20 according to the first embodiment. The setting apparatus 20c includes a condition rule storage unit 26c and a target condition setting unit 24, and further includes a condition rule setting unit 21c, a data input unit 22c, a content analyzing unit 23c, and a detection rule setting unit 25c.

The condition rule setting unit 21c sets a condition rule to output a target condition from the work instruction information and outputs it to the condition rule storage unit 26, like the condition rule setting unit 21 according to the first embodiment. As a characteristic feature, if the work instruction information includes the information of the target condition, the condition rule setting unit 21c automatically sets the condition rule. For example, assume that work instruction data is an incident report as shown in FIG. 12, and work instruction information includes a work category "inject the powder into the sack" and a cause of incident "the lever for fixing the sack is not down". In this case, the condition of the cause of the incident is defined as a target condition, thereby automatically setting the condition rule. For example, when the work category "inject the powder into the sack" is input, a condition rule to output a target condition "the lever for fixing the sack is not down" can automatically be set.

The data input unit 22c acquires work instruction data that is the input to the setting apparatus 20c, and outputs the work instruction data to the content analyzing unit 23c, like the data input unit 22 according to the first embodiment. However, the data input unit 22c can acquire work instruction data of a plurality of different forms. Furthermore, the data input unit 22c estimates or acquires the category of the input work instruction data, and outputs it to the content analyzing unit 23c. The categories of work instruction data are, for example, work instruction data, an incident report, and the like. The category of the work instruction data may be estimated by extracting a corresponding keyword in the work instruction data. Alternatively, the data input unit 22c may provide a GUI or physical keys used to input the category and cause the user of the system to input the category.

The content analyzing unit 23c analyzes the contents of the work instruction data, extracts work instruction information, and outputs it to the target condition setting unit 24 and the detection rule setting unit 25c, like the content analyzing unit 23 according to the first embodiment. Based on the category of the input work instruction data, the content analyzing unit 23c changes the work information to be extracted. For example, if the work instruction data is a work standard document, the content analyzing unit 23c extracts the category of the work, the work order, and notes during the work as work instruction information. In addition, if the work instruction data is an incident report, the content analyzing unit 23c extracts the category of the work and the category of the cause of the incident as work instruction information.

The method of extracting work information by the content analyzing unit 23c is not limited to a specific method. For example, when work instruction data of the form as shown in FIG. 11 is input, the content analyzing unit 23c extracts a text representing each work such as "extract a sack from the box" from the work list in the work instruction data, and converts it into a work category. As an example of the processing, a method of applying latent semantic analysis to a text representing a candidate of a work category and an input text of a work and making selection based on the similarity of latent meanings can be used. Note that as the work category, a work category defined in advance using the same GUI as the GUI shown in FIG. 2, which is provided by the condition rule setting unit 21 according to the first embodiment, is used. Next, the information of the work order is given to each converted work category. The information of the work category and the order is thus extracted as work instruction information. Note that the method of extracting the work information is not limited to the example described here, and the work information may be extracted by another method.

The detection rule setting unit 25c sets a detection rule based on the work instruction information input from the content analyzing unit 23c and the target condition input from the target condition setting unit 24, and outputs the detection rule to the detection rule storage device 1. As a characteristic feature, the detection rule according to this embodiment includes a work detection rule including a processing method of detecting a work in a video and a parameter and a condition detection rule to detect the target condition from the video of the work. At the time of detection, the work is detected based on the work detection rule, and the condition detection rule corresponding to the detected work is executed.

The processing method of the work detection rule is not limited to a specific method. For example, the work may be detected by applying an action recognition method or the work may be detected based on the information of a work schedule acquired from the work instruction information and time information. In addition, the condition detection rule is set like the condition detection rule according to the first embodiment.

With the above-described processing, the target condition during a work can be detected from a video based on work instruction data. It is also possible to automatically set a condition rule based on the work instruction data.

The embodiments described above can be applied to a monitoring system in a store. For example, assume that there exists a database that shares the information of shoplifting harm among a plurality of stores in the neighborhood. In this case, the monitoring system according to this embodiment acquires the information of shoplifting harm from the database, and sets a detection rule to detect a similar person based on the outer appearance of a shoplifter and features of actions. Accordingly, it is expected that shoplifting attempted by the same shoplifter in a neighboring store can be detected before it happens.

In addition, the present invention can also be implemented by executing the following processing. That is, software (program) that implements the functions of the above-described embodiments is supplied to the system or apparatus via a network or various kinds of storage media, and the computer (or CPU or MPU) of the system or apparatus reads out and executes the program.

As the industrial applicability of the present invention, the present invention can be used in a field to perform detection from a video such as watching in a hospital or a care facility, a monitoring system, and increasing the productivity in a factory.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-065498, filed Mar. 29, 2018 which is hereby incorporated by reference herein in its entirety.

What is claimed is:

1. An information processing apparatus for monitoring an object in a video, comprising:
a first storage unit configured to store a plurality of pieces of rule information defining a target part and a moving amount of the target part to be detected in a condition;
a second storage unit configured to store a plurality of IDs each specifying an object and the rule information corresponding to each of the plurality of IDs;
a third storage unit configured to store a plurality of IDs each specifying an object and feature data for recognizing each of the objects;
an input unit configured to input information identifying a monitored object and information representing a condition of the monitored object;
an acquiring unit configured to acquire, from the first storage unit, the rule information defining the target part and the moving amount of the target part using the condition inputted by the input unit, as the rule information corresponding to the monitored object;
a determination unit configured to receive, from a camera, a video captured by the camera, detect an object in the video and determine whether the detected object in the video is the monitored object using the information identifying the monitored object inputted by the input unit; and
an output unit configured to, if the determination unit determines that the detected object in the video is the monitored object, determine whether the detected object in the video moves the target part more than the moving amount, which is represented by the rule information acquired by the acquiring unit, and output a result of the determination,
wherein the input unit inputs the condition of the monitored object and an ID of the monitored object,
wherein the acquiring unit registers the ID of the monitored object input by the input unit and the rule information acquired from the first storage unit based on the condition of the monitored object into the second storage unit, and
wherein the determination unit acquires an ID of an object in the video by recognizing the object in the video by referring to the third storage unit, determines whether the second storage unit stores an ID matching with the acquired ID, and determines that the object in the video is the monitored object if it is determined that the second storage unit stores the ID matching with the acquired ID.

2. The apparatus according to claim 1, wherein the monitored object is a person, and the condition of the monitored object includes a health condition.

3. The apparatus according to claim 2, wherein a movement indicated by the rule information includes a dangerous movement.

4. The apparatus according to claim 3, wherein the rule information includes a threshold of a danger level, and defines a movement which exceeds the threshold as the dangerous movement.

5. The apparatus according to claim 2, wherein the input unit analyzes medical data and inputs the health condition.

6. The apparatus according to claim 2, further comprising a patient database configured to store information used to identify a patient, wherein the output unit refers to the patient database based on feature information obtained from an image of the person in the video received from the camera, determines whether the person in the video is a patient, and upon determining that the person is a patient, starts monitoring the person in the video.

7. The apparatus according to claim 1, wherein a health condition includes a disease name.

8. The apparatus according to claim 1, wherein the monitored object is one of a person and a machine, and the condition of the monitored object is a stage of a work.

9. The apparatus according to claim 8, wherein a movement indicated by the rule information includes an abnormal movement.

10. The apparatus according to claim 1, wherein the rule information includes an allowable range for a movement and defines a movement which exceeds the allowable range as the movement to be detected.

11. The apparatus according to claim 1, wherein the rule information includes a restriction/prohibition for a movement and defines a movement which violates the restriction/prohibition as the movement to be detected.

12. The apparatus according to claim 1, further comprising a correction unit configured to correct the rule information.

13. The apparatus according to claim 12, wherein the correction unit is further configured to correct the rule information after a predetermined period.

14. The apparatus according to claim 12, wherein the correction unit is further configured to correct the rule information based on an image capturing environment of the video.

15. The apparatus according to claim 1, wherein the rule information is described in a text form.

16. The apparatus according to claim 1, further comprising a creating unit configured to set and create the rule information.

17. The apparatus according to claim 1, wherein in a case in which the monitored object moves the target part more than the moving amount which is represented by the rule information acquired by the acquiring unit, the output unit outputs, to a terminal set in advance, information representing that the condition to be detected is obtained.

18. A method of controlling an information processing apparatus that includes a first storage unit configured to store a plurality of pieces of rule information defining a target part and a moving amount of the target part to be detected in a condition, a second storage unit configured to store a plurality of IDs each specifying an object and the rule information corresponding to each of the plurality of IDs, and a third storage unit configured to store a plurality of IDs each specifying an object and feature data for recognizing each of the objects, and that monitors an object in a video, the method comprising:

inputting information identifying a monitored object and information representing a condition of the monitored object;

acquiring, from the first storage unit, the rule information defining the target part and the moving amount of the target part using the condition inputted in the inputting, as rule information corresponding to the monitored object;

receiving, from a camera, a video captured by the camera, detecting an object in the video and determining whether the detected object in the video is the monitored object using the information identifying the monitored object inputted in the inputting; and if it is determined that the detected object in the video is the monitored object, determining whether the detected object in the video moves the target part more than the moving amount, which is represented by the acquired rule information and outputting a result of the determination, wherein in the inputting, the condition of the monitored object and an ID of the monitored object are inputted, wherein in the acquiring, the ID of the monitored object inputted in the inputting and the rule information acquired from the first storage unit based on the condition of the monitored object are registered into the second storage unit, and wherein in the determining, an ID of an object in the video by recognizing the object in the video is acquired by referring to the third storage unit, it is determined whether the second storage unit stores an ID matching with the acquired ID, and it is determined that the object in the video is the monitored object if it is determined that the second storage unit stores the ID matching with the acquired ID.

19. A non-transitory computer-readable storage medium storing a program which causes, when executed by a computer, the computer to execute steps of a method of controlling an information processing apparatus that includes a first storage unit configured to store a plurality of pieces of rule information defining a target part and a moving amount of the target part of an object to be detected in a condition, a second storage unit configured to store a plurality of IDs each specifying an object and the rule information corresponding to each of the plurality of IDs, and a third storage unit configured to store a plurality of IDs each specifying an object and feature data for recognizing each of the objects, and that monitors an object in a video, the method comprising:

inputting information identifying a monitored object and information representing a condition of the monitored object;

acquiring, from the first storage unit, the rule information defining the target part and the moving amount of the target part using the condition inputted in the inputting;

receiving, from a camera, a video captured by the camera, detecting an object in the video, and determining whether the detected object in the video is the monitored object; and if it is determined that the detected object in the video is the monitored object, determining whether the detected object in the video moves the target part more than the moving amount, which is represented by the acquired rule information and outputting a result of the determination, wherein in the inputting, the condition of the monitored object and an ID of the monitored object are inputted, wherein in the acquiring, the ID of the monitored object inputted in the inputting and the rule information acquired from the first storage unit based on the condition of the monitored object are registered into the second storage unit, and wherein in the determining, an ID of an object in the video by recognizing the object in the video is acquired by referring to the third storage unit, it is determined whether the second storage unit stores an ID matching with the acquired ID, and it is determined that the object in the video is the monitored object if it is determined that the second storage unit stores the ID matching with the acquired ID.

20. A monitoring system for monitoring an object in a video, the monitoring system comprising:
   at least one image capturing device configured to capture the object; and
   a monitoring device configured to monitor the object, wherein the monitoring device comprises:
      a communication unit configured to receive a video captured by the at least one image capturing device;
      a first storage unit configured to store a plurality of pieces of rule information defining a target part and a moving amount of the target part to be detected in a condition;
      a second storage unit configured to store a plurality of IDs each specifying an object and the rule information corresponding to each of the plurality of IDs;
      a third storage unit configured to store a plurality of IDs each specifying an object and feature data for recognizing each of the objects;
      an input unit configured to input information identifying a monitored object and information representing a condition of the monitored object;
      an acquiring unit configured to acquire, from the first storage unit, the rule information defining the target part and the moving amount of the target part using the condition inputted by the input unit, as rule information corresponding to the monitored object;
      a determination unit configured to receive, from the at least one image capturing device, the video captured by the at least one image capturing device, detect an object in the video and determine whether the detected object in the video is the monitored object using the information identifying the monitored object; and
      an outputting unit configured to, if the determination unit determines that the detected object in the video is the monitored object, determine whether the detected object in the video moves the target part more than the moving amount, which is represented by the rule information acquired by the acquiring unit, and output a result of the determination,
   wherein the input unit inputs the condition of the monitored object and an ID of the monitored object,
   wherein the acquiring unit registers the ID of the monitored object input by the input unit and the rule information acquired from the first storage unit based on the condition of the monitored object into the second storage unit, and
   wherein the determination unit acquires an ID of an object in the video by recognizing the object in the video by referring to the third storage unit, determines whether the second storage unit stores an ID matching with the acquired ID, and determines that the object in the video is the monitored object if it is determined that the second storage unit stores the ID matching with the acquired ID.

* * * * *